US010105466B2

United States Patent
Hong et al.

(10) Patent No.: US 10,105,466 B2
(45) Date of Patent: *Oct. 23, 2018

(54) COMPOSITIONS WITH REACTIVE INGREDIENTS, AND WOUND DRESSINGS, APPARATUSES, AND METHODS

(71) Applicant: KCI Licensing, Inc., San Antonio, TX (US)

(72) Inventors: KZ Hong, San Antonio, TX (US); Shannon C. Ingram, Bulverde, TX (US); Dmitry Zimnitsky, San Antonio, TX (US); Justin Alexander Long, San Antonio, TX (US); Richard M. Kazala, Jr., San Antonio, TX (US); Hugo Ramirez, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1001 days.

This patent is subject to a terminal disclaimer.

(21) Appl. No.: 14/257,261

(22) Filed: Apr. 21, 2014

(65) Prior Publication Data

US 2014/0343514 A1     Nov. 20, 2014

Related U.S. Application Data

(63) Continuation of application No. 13/085,041, filed on Apr. 12, 2011, now Pat. No. 8,785,713.

(Continued)

(51) Int. Cl.
*A61M 35/00* (2006.01)
*A61L 26/00* (2006.01)

(Continued)

(52) U.S. Cl.
CPC .... *A61L 26/0095* (2013.01); *A61F 13/00068* (2013.01); *A61F 13/00072* (2013.01); *A61K 33/00* (2013.01); *A61L 15/425* (2013.01); *A61M 1/0084* (2013.01); *A61M 1/0088* (2013.01); *A61F 2013/0017* (2013.01);

(Continued)

(58) Field of Classification Search
CPC .. A61L 26/0095; A61L 25/425; A61L 15/425; A61F 13/00068; A61F 13/00072
See application file for complete search history.

(56) References Cited

U.S. PATENT DOCUMENTS 1,355,846 A    10/1920   Rannells
1,867,222 A *   7/1932   Karns .................... A61L 15/18
                                                    424/443

(Continued)

FOREIGN PATENT DOCUMENTS

AU        550575 A1    3/1986
AU        745271        4/1999

(Continued)

OTHER PUBLICATIONS

Supplementary European Search Report Application No. 11769422 dated Jun. 19, 2014.

(Continued)

*Primary Examiner* — Kim M Lewis

(57) ABSTRACT

Wound dressings and wound inserts comprising substantially dry reactive agents, methods of forming wound inserts comprising dry reactive agents, and wound-treatment methods.

5 Claims, 13 Drawing Sheets

Related U.S. Application Data

(60) Provisional application No. 61/323,663, filed on Apr. 13, 2010.

(51) Int. Cl.

| | | |
|---|---|---|
| *A61L 15/42* | (2006.01) | |
| *A61M 1/00* | (2006.01) | |
| *A61K 33/00* | (2006.01) | |
| *A61F 13/00* | (2006.01) | |

(52) U.S. Cl.
CPC ............... *A61F 2013/0091* (2013.01); *A61F 2013/00174* (2013.01); *A61F 2013/00536* (2013.01); *A61M 35/00* (2013.01); *A61M 2205/7536* (2013.01)

(56) References Cited

U.S. PATENT DOCUMENTS

| | | | |
|---|---|---|---|
| 2,087,633 A * | 7/1937 | Wales | B65D 83/0805 118/123 |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,888,225 A * | 12/1989 | Sandvig | A43D 999/00 168/12 |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,296,518 A | 3/1994 | Grasel et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,898,040 A | 4/1999 | Shalaby et al. | |
| 6,042,817 A | 3/2000 | Polunsky et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,387,384 B1 | 5/2002 | Probert et al. | |
| 6,398,767 B1 * | 6/2002 | Fleischmann | A61M 1/0088 604/304 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2009/0057017 A1 | 3/2009 | Berger et al. | |
| 2011/0021964 A1 * | 1/2011 | Larsen | A61L 26/0066 602/47 |
| 2011/0144182 A1 * | 6/2011 | Becker | A61K 9/0014 514/44 A |
| 2011/0184357 A1 * | 7/2011 | Robinson | A61F 13/00068 604/290 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 606431 | 8/1948 |

(56) References Cited

FOREIGN PATENT DOCUMENTS

| | | |
|---|---|---|
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | H4-312458 | 11/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 01047705 A1 | 7/2001 |
| WO | 2005070480 A1 | 8/2005 |
| WO | 2008032697 A1 | 3/2008 |
| WO | 2008040020 A2 | 4/2008 |
| WO | 2008091521 A2 | 7/2008 |

OTHER PUBLICATIONS

A. Gabriel et al.: "A Clinical Review of Infected Wound Treatment with Vacuum Assisted Closure (V.A.C.) Therapy: Experience and Case Series", Int Wound Journal vol. 6 (suppl. 2), Jan. 1, 2009, pp. 1-25 XP055124010.
Chemical Dictionary 4, Kyoritsu Shuppan Co. Ltd., 1987, 30th Pocket Edition. p. 3-5.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Extended European Search Report for corresponding Application No. 181691163, dated Aug. 8, 2018.

\* cited by examiner

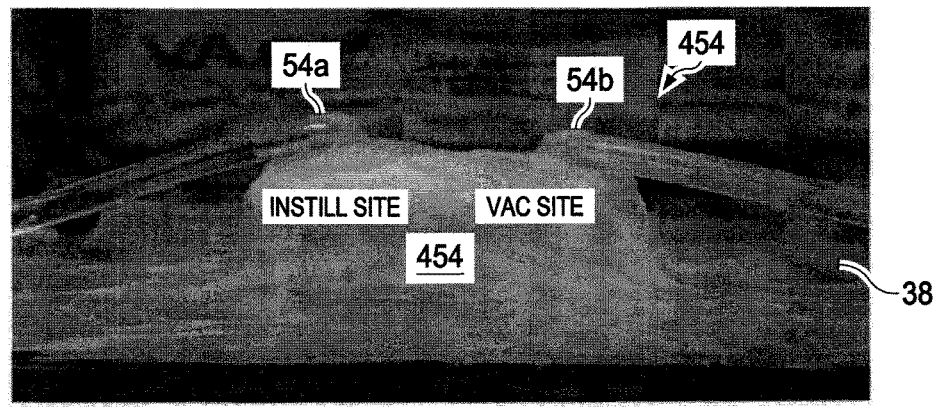
FIG. 13A
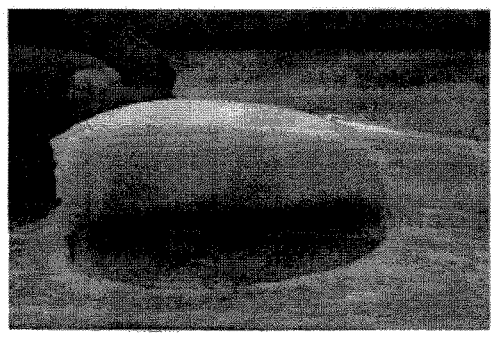 
FIG. 13B  FIG. 13C
 
FIG. 13D  FIG. 13E

US 10,105,466 B2

COMPOSITIONS WITH REACTIVE INGREDIENTS, AND WOUND DRESSINGS, APPARATUSES, AND METHODS

CROSS-REFERENCE TO RELATED APPLICATIONS

This application is a continuation of U.S. application Ser. No. 13/085,041, filed Apr. 12, 2011 which claims priority to U.S. Provisional Patent Application No. 61/323,663, filed Apr. 13, 2010, which is incorporated herein in its entirety.

BACKGROUND

1. Field of the Invention

The present invention relates generally to healing of wounds and wound-treatment therapies. More particularly, but not by way of limitation, the present invention relates to fluid-instillation and negative-pressure wound therapies, comprising a foam (and/or other porous material) wound insert containing reactive agents.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation of fluids (e.g., irrigation fluids and/or medicaments) may be used in conjunction with negative pressure wound therapy to promote healing and/or improve efficacy. One example of a system for delivering active solutions to a wound is disclosed in U.S. Pat. No. 6,398,767.

SUMMARY

The present disclosure includes embodiments of wound inserts, wound dressings, methods of forming wound inserts, and wound-treatment methods.

Some embodiments of the present wound inserts are for use between a wound of a patient and a drape coupled to skin around the wound such that the drape covers the wound and forms a space between the drape and the wound. Some embodiments of the present wound inserts comprise: an open-celled foam (e.g., configured to be disposed between a wound of a patient and a drape coupled to skin adjacent the wound, e.g., such that the drape forms a space between the wound and the drape); and a reactive agent disposed within the foam, and configured to be inert in the absence of an activating fluid and to exhibit antimicrobial properties when released by an activating fluid.

In some embodiments, the reactive agent is configured to react with water (and/or aqueous solution) to release hypochlorite ion and/or form hypochlorous acid, depending on pH. In some embodiments, the reactive agent comprises a hypochlorite salt. In some embodiments, the reactive agent comprises a substance defined by M(OCl)n, where n=1 if M is $K^+$, $Li^+$, or $Na^+$, and where n=2 if M is $Ca^{2+}$ or $Mg^{2+}$. In some embodiments, the reactive agent comprises at least one of: an N-chloro taurine; an N,N-dichloro taurine; an N-halogenated amino acid; an N,N-dihalogenated amino acid; or a combination of any two or more of these. Some embodiments comprise (alternatively or additionally) an agent comprising a growth factor; a protein; a peptide; or a combination thereof.

In some embodiments, the wound insert comprises a suspension agent including at least one of: a polyvinylpyrrolidone, a polyethylene oxide, a polyvinyl acetate (PVA), a polyvinyl alcohol (PVOH), an ethylene vinyl alcohol (EVOH) copolymer, an ethylene styrene copolymer, polycaprolactone (PCL), polysorbate, or a combination of any two or more of these. In some embodiments, the suspension agent couples the reactive agent to the foam. In some embodiments, the suspension agent encapsulates the reactive agent. In some embodiments, the suspension agent is configured to dissolve in the presence of a solvent. In some embodiments, the suspension agent is water soluble. In some embodiments, the wound insert is configured to release a hypochlorite ion in the presence of a volume of activating liquid such that after release the volume of activating liquid will have a concentration of hypochlorite ion between 0.7 and 20 millimolar. In some embodiments, the wound insert is configured to release a hypochlorite ion in the presence of each of three or more sequential volumes of activating liquid such that after release each sequential volume of activating liquid will have a concentration of hypochlorite ion between 0.7 and 20 millimolar.

In some embodiments, the reactive agent is dispersed throughout at least a portion of the foam. In some embodiments, the foam comprises silicone polymer. In some embodiments, the foam comprises a fluoropolymer. In some embodiments, the fluoropolymer comprises at least one of: polytetrafluoroethylene (PTFE), polyvinylidene fluoride (PVDF), perfluoroalkoxy (PFA) polymer, fluoroethylkene (FEP), or a combination of any two or more of these. In some embodiments, the foam comprises at least one of a polyolefin or polyolefin copolymer. In some embodiments, the polyolefin includes at least one of: polyethylene (PE), polypropylene (PP), polybutylene (PB), ethylene-vinyl acetate (EVA), copolymers of any of these or a combination of any two of these.

Some embodiments further comprise: a second open-celled foam that is not coupled to the reactive agent; where the first open-celled foam is configured to be inert in the present of the reactive agent, and forms a first layer of the wound insert; and where the second open-celled foam forms a second layer of the wound insert, and is coupled to the first open-celled foam.

Some embodiments of the present wound inserts comprise: an open-celled foam configured to be disposed between a wound of a patient and a drape coupled to skin adjacent the wound (e.g., such that the drape forms a space between the wound and the drape), the foam having an upper side and lower side configured to face the wound; a plurality of particles of a first metal dispersed within the foam; and a second metal coupled to the lower side of the foam, and configured such that a fluid can be introduced to generate microcurrents between the first metal and the second metal.

In some embodiments, the first metal is dispersed in the foam such that if a fluid passes through the foam at least some portion of the first metal will exit the foam.

Some embodiments further comprise: a permeable layer coupled to the lower side of the foam; where the second metal is coupled to the permeable layer. In some embodiments, the wound insert is configured such that if a fluid is passed through the foam from the upper side through the lower side, at least some portion of the first metal will exit the foam through the lower side and pass through the permeable layer. In some embodiments, the wound insert is configured such that if the wound insert is disposed such that the permeable layer is in contact with a wound and a fluid is passed through the foam from the upper side to the lower side, at least some portion of the first metal will exit the foam through the permeable layer and microcurrents will be generated between the first metal and the second metal coupled to the permeable layer. In some embodiments, the first metal comprises silver. In some embodiments, the second metal comprises zinc.

In some embodiments, the present wound inserts are in combination with a drape configured to be coupled to skin adjacent a wound of a patient. In some embodiments, the present wound inserts are in combination with a fluid delivery pad configured to be coupled to the drape and a fluid source such that the fluid source is actuatable to deliver a fluid to a wound through the wound dressing. In some embodiments, the present wound inserts are in combination with a fluid source configured to be coupled to the wound dressing such that the fluid source is actuatable to deliver a fluid to the wound dressing. In some embodiments, the present wound inserts are in combination with a vacuum source configured to be coupled to the wound dressing such that the vacuum source is actuatable to apply negative pressure to the wound dressing.

Some embodiments of the present wound dressings comprise: one or more of any of the present wound inserts; and a drape configured to be coupled to skin adjacent a wound of a patient (e.g., such that the drape covers the wound insert and forms a space between the wound and the drape). Some embodiments further comprise: a fluid delivery pad configured to be coupled to the drape and a fluid source such that the fluid source is actuatable to deliver a fluid to a wound through the wound dressing.

Some embodiments of the present wound-treatment apparatuses comprise: a wound dressing with a drape and one or more of any of the present wound inserts; and a fluid source configured to be coupled to the wound dressing such that the fluid source is actuatable to deliver a fluid to the wound dressing. Some embodiments further comprise: a vacuum source configured to be coupled to the wound dressing such that the vacuum source is actuatable to apply negative pressure to the wound dressing.

Some embodiments of the present methods comprise: adding (e.g., dry) hypochlorite salt particles to a solution such that the solution and hypochlorite salt form a slurry, the solution comprising a polymer and a liquid that is a solvent of the polymer but not a solvent of the hypochlorite salt; and substantially removing the liquid from the slurry such that at least a portion of the hypochlorite salt particles are at least partially encapsulated by the polymer. In some embodiments, the hypochlorite salt is defined by M(OCl)n, where n=1 if M is $K^+$, $Li^+$, or $Na^+$, and where n=2 if M is $Ca^{2+}$ or $Mg^{2+}$. In some embodiments, the hypochlorite salt is defined by $Ca(OCl)_2$. In some embodiments, the polymer is biocompatible and optionally biodegradable. In some embodiments, the polymer is not water soluble. In some embodiments, the polymer comprises polycaprolactone (PCL). In some embodiments, the solvent is non-aqueous. In some embodiments, the solvent comprises at least one of Dichloromethane (DCM or methylene chloride), Tetrahydrofuran (THF), or Cyclohexane. Some embodiments further comprise: disposing, prior to substantially removing the liquid, a foam in the slurry such that hypochlorite salt particles and polymer are dispersed within the foam. Some embodiments further comprise: reducing, prior to adding the hypochlorite salt particles into the solution, the size of the hypochlorite salt particles such that a majority of the hypochlorite salt particles have a size at or below a target size. In some embodiments, the target size is 180 microns.

Some embodiments of the present methods of forming a wound insert comprise: applying negative pressure to an open-celled foam to draw particles into the foam such that the particles become dispersed throughout at least a portion of the foam. In some embodiments, the foam has a first side and a second side opposite the first side, and the method further comprises: disposing the foam between a filter configured and a particle reservoir such that the filter is adjacent the first side of the foam and the reservoir is adjacent the second side, the filter configured to substantially prevent passage of the particles through the filter; and where applying negative pressure comprises applying negative pressure to the filter such that the particles are drawn from the reservoir into the foam.

In some embodiments, the particles comprise a reactive agent. In some embodiments, the reactive agent is configured to react with water (and or aqueous solution) to release hypochlorite ion and/or form hypochlorous acid, depending on pH. In some embodiments, the reactive agent comprises hypochlorite. In some embodiments, the reactive agent comprises a substance defined by M(OCl)n, where n=1 if M is $K^+$, $Li^+$, or $Na^+$, and where n=2 if M is $Ca^{2+}$ or $Mg^{2+}$. In some embodiments, the reactive agent comprises at least one of: an N-chloro taurine; an N,N-dichloro taurine; an N-halogenated amino acid; an N,N-dihalogenated amino acid; or a combination of any two or more of these. Some embodiments comprise (alternatively or additionally) an agent comprising a growth factor; a protein; a peptide; or a combination thereof. In some embodiments, the particles comprise a metal. In some embodiments, the particles comprise silver.

In some embodiments, the particles comprise a suspension agent including at least one of: a polyvinylpyrrolidone, a polyethylene oxide, a polyvinyl acetate (PVA), a polyvinyl alcohol (PVOH), an ethylene vinyl alcohol (EVOH) copolymer, an ethylene styrene copolymer, polycaprolactone (PCL), polysorbate, or a combination of any two or more of these. In some embodiments, the suspension agent is configured to bind the reactive agent to the foam. In some embodiments, the suspension agent encapsulates the reactive agent. In some embodiments, the suspension agent is configured to dissolve in the presence of a solvent. In some embodiments, the suspension agent is water soluble.

In some embodiments, the foam comprises silicone polymer. In some embodiments, the foam comprises a fluoropolymer. In some embodiments, the fluoropolymer comprises at least one of: polytetrafluoroethylene (PTFE), polyvinylidene fluoride (PVDF), perfluoroalkoxy (PFA) polymer, fluoroethylkene (FEP), or a combination of any two or more of these. In some embodiments, the foam comprises at least one of a polyolefin or polyolefin copolymer. In some embodiments, the polyolefin includes at least one of: polyethylene (PE), polypropylene (PP), polybutylene (PB), ethylene-vinyl acetate (EVA), copolymers of any of these, or a combination of any two of these.

Some embodiments of the present wound-treatment methods comprise: delivering a fluid to a wound through a wound dressing comprising: a drape coupled to skin adjacent a wound of a patient (e.g., such that the drape covers the wound and forms a space between the drape and the wound); an open-celled foam wound insert disposed between the drape and the wound (e.g., in the space); and a reactive agent dispersed throughout at least a portion of the wound inserts such that upon delivery of the fluid to the wound insert the fluid causes at least a portion of the reactive agent to pass from the wound insert to the wound. In some embodiments, delivering a fluid comprises activating a fluid source that is coupled to the wound dressing to deliver the fluid to the wound through the wound dressing. Some embodiments further comprise: applying negative pressure to the wound through the wound dressing. In some embodiments, applying negative pressure comprises activating a vacuum source that is coupled to the wound dressing to apply the vacuum to the wound through the wound dressing.

Some embodiments of the present wound-treatment methods comprise: delivering a fluid to a wound through a wound dressing comprising: a drape coupled to skin adjacent a wound of a patient (e.g., such that the drape covers the wound and forms a space between the drape and the wound); an open-celled foam wound insert disposed between the drape and the wound (e.g., in the space); and a plurality of particles of a first metal dispersed within the foam; a second metal coupled to the lower side of the foam, and configured such that upon delivery of the fluid microcurrents are generated between the first metal and the second metal. In some embodiments, the first metal is dispersed in the foam such that when the fluid is delivered it passes through the foam and at least some portion of the first metal exits the foam.

In some embodiments, the wound dressing further comprises: a permeable layer coupled to a lower side of the wound insert; and where the second metal is coupled to the permeable layer. In some embodiments, the wound dressing is configured such that upon delivery of the fluid to the wound dressing the fluid passes through the wound insert from an upper side through the lower side, and at least some portion of the first metal exits the foam through the lower side and passes through the permeable layer. In some embodiments, the wound insert is disposed such that the permeable layer is in contact with the wound such that upon delivery of the fluid to the wound dressing the fluid passes through the foam from the upper side to the lower side, at least some portion of the first metal exits the foam through the permeable layer and microcurrents are generated between the first metal and the second metal coupled to the permeable layer. In some embodiments, the first metal comprises silver. In some embodiments, the second metal comprises zinc.

Some embodiments of the present wound inserts comprise: an open-celled and/or hydrophilic foam configured to be disposed between a wound of a patient and a drape coupled to skin adjacent the wound (e.g., such that the drape forms a space between the wound and the drape); and a liquid solution comprising an antimicrobial agent, the liquid solution disposed within the foam. In some embodiments, the foam comprises a PVOH foam. In some embodiments, the antimicrobial agent comprises polyhexanide. Some embodiments comprise a container enclosing the foam and configured to prevent evaporation of the liquid solution. In some embodiments, the container comprises a foil pouch. In some embodiments, the container comprises a plastic pouch.

Some of the present embodiments include an open-celled foam wound insert comprising a reactive agent disposed within the wound insert, and configured to be inert in the absence of an activating fluid and to exhibit antimicrobial properties in the presence of an activating fluid, for use in a wound treatment method comprising the step of delivering a fluid to a wound through a wound dressing comprising: a drape coupled to skin adjacent a wound of a patient such that the drape covers the wound and forms a space between the drape and the wound; the insert disposed in the space; and where the wound insert is configured such that when the fluid is delivered to the wound insert, at least a portion of the reactive agent passes from the wound insert to the wound. Such embodiments may optionally include any features described herein in relation to other embodiments, such as, for example, the features described in relation to methods of treatment.

Some of the present embodiments include a reactive agent configured to be inert in the absence of an activating fluid and to exhibit antimicrobial properties in the presence of an activating fluid, for use in a wound treatment method comprising the step of delivering a fluid to a wound through a wound dressing comprising: a drape coupled to skin adjacent a wound of a patient such that the drape covers the wound and forms a space between the drape and the wound; the insert disposed in the space; and the reactive agent disposed within the wound insert, and configured to be inert in the absence of an activating fluid and to exhibit antimicrobial properties in the presence of an activating fluid; where the wound insert is configured such that when the fluid is delivered to the wound insert, at least a portion of the reactive agent passes from the wound insert to the wound. Such embodiments may optionally include any features described herein in relation to other embodiments, such as, for example, those features described in relation to methods of treatment.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 13A-13E depict photographs illustrating tests performed on various foams to determine stability of the foams in contact with hypochlorous acid solution.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound-treatment method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises one of the present wound inserts and a drape, the wound dressing includes the specified elements but is not limited to having only those elements. For example, such a wound dressing could also include a connection pad configured to be coupled to a negative pressure wound therapy (NPWT) apparatus (e.g., including a vacuum source and/or a fluid source).

Further, a device or structure that is configured in a certain way is configured in at least that way, but it may also be possible for it to be configured in other ways than those specifically described.

Figure 1:
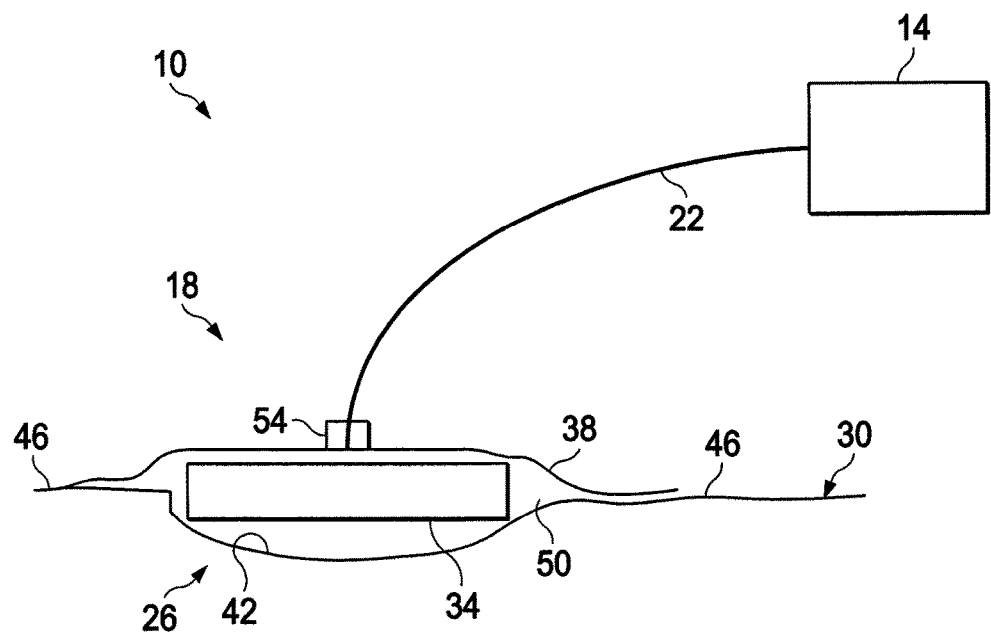
FIG. 1 depicts a side view of one of the present wound dressings having one of the present wound inserts and coupled to a wound site and to a wound treatment apparatus.

Referring now to the drawings, and more particularly to FIG. 1, shown therein is an embodiment of one of the present wound treatment system 10. In the embodiment shown, apparatus 10 comprises a wound-treatment apparatus 14, and a wound dressing 18. In the embodiment shown, apparatus 14 is coupled to wound dressing 18 by a conduit 22. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and drape 38 is configured to be coupled to (and is shown coupled to) skin 46 of the patient adjacent to wound 26 such that drape 38 covers wound insert 34 and wound 26 (e.g., such that drape 38 forms a space 50 between drape 38 and wound 26 (e.g., wound surface 42)).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., and instillation fluid such as a medicinal fluid, antibacterial fluid, irrigation fluid, and or the like) to wound dressing 18. System 10 can be implemented and/or actuated and/or coupled to patient 30 in any of various configurations and/or methods described in this disclosure. Additionally, various wound therapy systems and components are commercially available through and/or from KCI USA, Inc. of San Antonio, Tex., U.S.A.

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCl. One example of a suitable drape 38 includes the "V.A.C.® Drape" commercially available from KCI. Another example of a connection pad 54 is disclosed in U.S. patent application Ser. No. 11/702,822, incorporated above.

Figure 2:
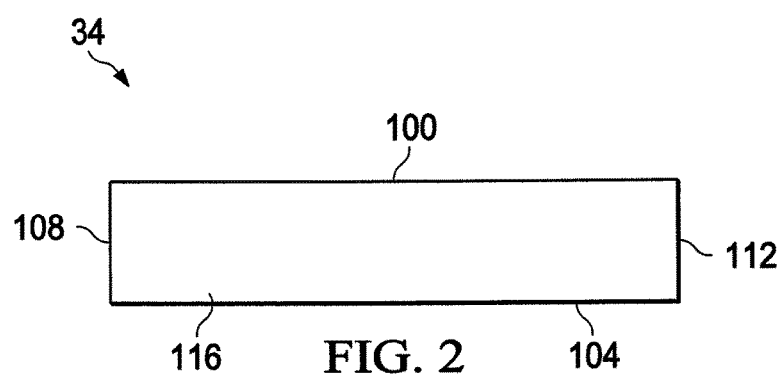
FIG. 2 depicts an enlarged side view of the wound insert of FIG. 1.

Referring now to FIG. 2, a side view of a wound insert 34 is shown. Wound insert 34 has an upper side 100, a lower side 104, lateral sides 108, 112 and interior volume 116. Although one side is shown of wound insert 34, it will be understood by those of ordinary skill in the art to wound insert 34 includes a three-dimensional, rectangular volume (shown with rectangular faces) having a depth extending perpendicular to the side shown. In other embodiments, wound insert 34 can have a suitable shape, such as, for example, a round cylindrical shape, a fanciful shape, or may be trimmed to fit an irregular shape of a wound (e.g., 26 and/or wound surface 42). Wound insert 34 may comprise a foam, such as, for example, an open-celled (and/or reticulated) foam.

Embodiments of the present wound treatment methods may be better understood with reference to FIG. 3, which depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and/or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. In this way pressure sensor 212 can sense and/or detect the negative pressure in wound dressing 18 and/or any of the various conduits coupled wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240. In the embodiment shown canister 204 can comprise a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 is typically configured such that during operation vacuum source 200 will provide sufficient airflow through filter 244 that the pressure drop across filter 244 is not substantial (e.g., such that the pressure drop will not substantially interfere with the application of negative pressure to wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and with like such that communication can be selectively permitted between wound dressing 18 and vacuum source 200, or between wound dressing 18 and fluid source 248. In some embodiments apparatus 14 comprises only one of vacuum source 200 and fluid source 248. In embodiments of apparatus 14 that comprise only fluid source 248, canister 204 and/or pressure sensor 212 can also be omitted. Various embodiments, such as the one shown, conduit 232 and/or conduit 240 and/or conduit 252 can be combined and/or comprised in a single multi-lumen conduit, such as is described above with reference to FIG. 1. In various embodiments, such as the one shown in FIG. 3A, apparatus 14 can be configured such that as soon as the liquid in the canister reaches a level where filter 244 is occluded, a much-increased negative (or subatmospheric) pressure occurs in conduit 208 and is detected by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply intermittent negative (or subatmospheric) pressure to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site (to allow pressure at the wound site to equalize with atmospheric pressure), and then close to restore the negative pressure (allow the pump to restore negative pressure at the wound site). It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is detected by transducer 216. This saves power and enables the appliance to operate for long periods on its battery power supply.

Figure 3A:
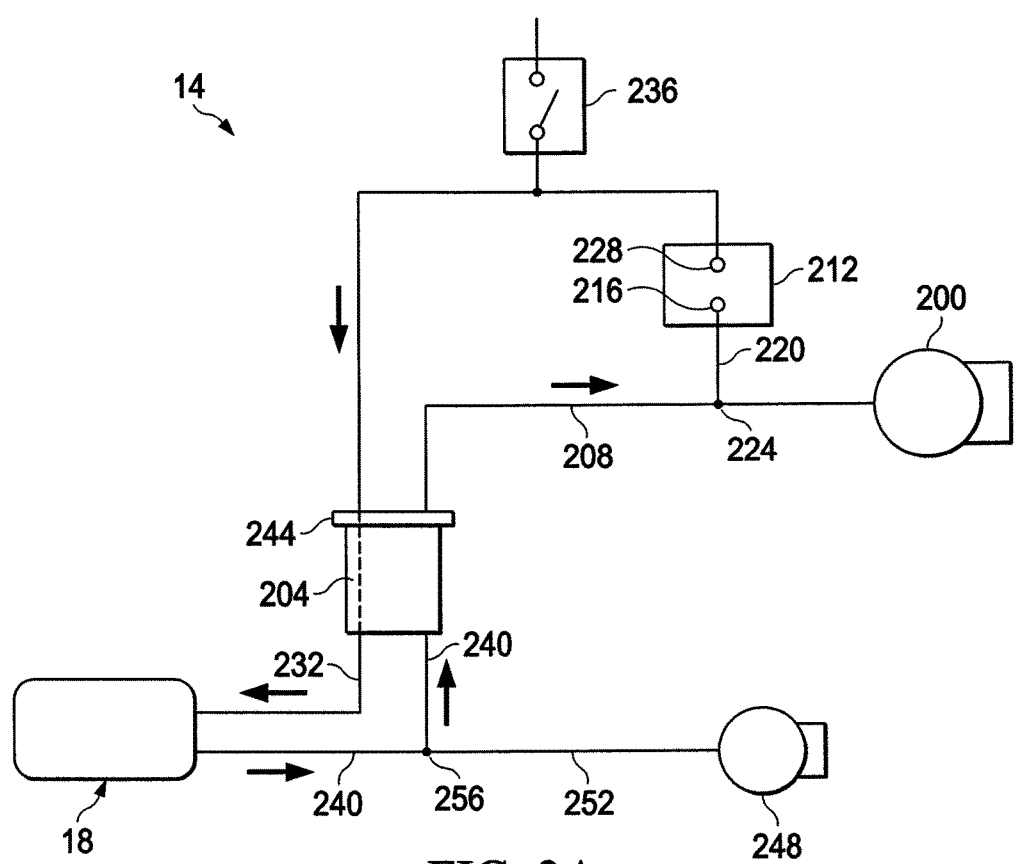
FIG. 3A depicts a schematic block diagram of one embodiment of a wound treatment apparatus that can comprise and/or be coupled to and/or be used with the present wound dressings and/or wound inserts.
Figure 3B:
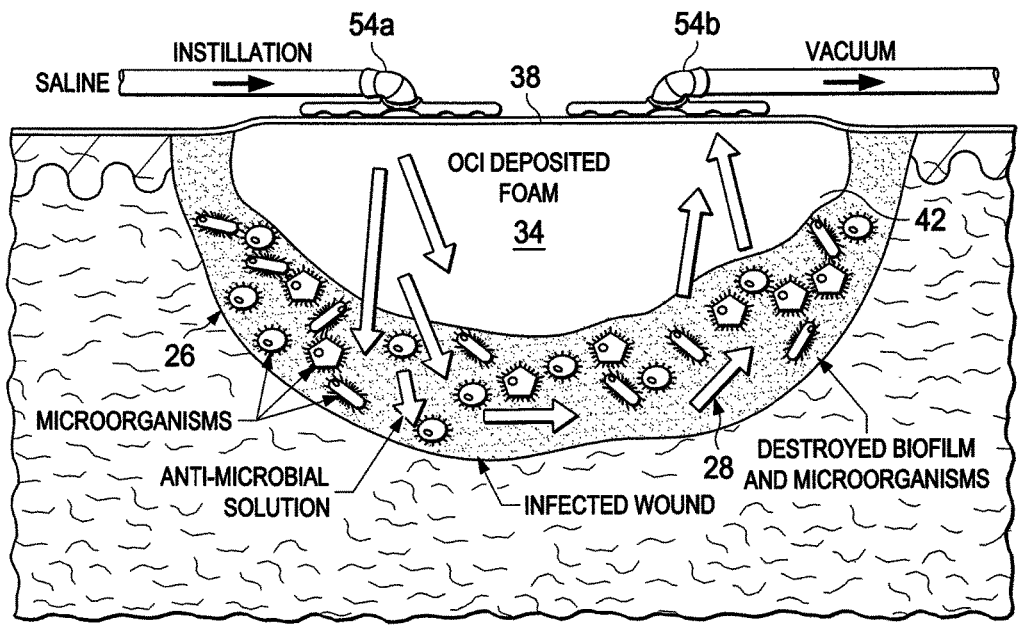
FIG. 3B depicts an enlarged cross-sectional view of one of the present wound dressings coupled to a wound.

FIG. 3B depicts an enlarged cross-sectional view of one of the present wound dressings 18 coupled to wound 26. In FIG. 3B, wound 26 is illustrated as an infected wound having a plurality of microorganisms 28 (e.g., bacteria) or biofilm infecting wound surface 42 and/or a depth of tissue beneath wound surface 42. More particularly, and as described above for FIG. 1, wound dressing 18 comprises wound insert 34 disposed adjacent or on wound 26 (e.g., wound surface 42), and drape 38 coupled to skin 46 adjacent wound 26 such that drape 38 covers wound insert 34 and wound 26 and forms a space 50 between wound surface 42 and drape 38. In the embodiment shown, a first connection pad 54a is coupled to drape 38 and configured to be coupled to a fluid source (e.g., 248) by a fluid conduit (e.g., 252) such that the fluid source can be activated to deliver a fluid (e.g., saline) to wound 26 (e.g., wound surface 42) through wound dressing 18; and a second connection pad 54b is coupled to drape 38 and configured to be coupled to a vacuum source (e.g., 200) by a conduit (e.g., 240) such that the vacuum source can be activated to apply negative pressure to wound 26 (e.g., wound surface 42) through wound dressing 18. Wound insert 34 comprises an open-celled foam that is configured to be (and is shown) disposed between wound 26 and drape 38. Additionally, in the embodiment shown, wound insert 34 comprises a reactive agent deposited on or in (e.g., dispersed throughout at least a portion of) wound insert 34 such that upon delivery of a fluid to wound insert 34 the fluid reacts with and/or causes at least a portion of the reactive agent to pass from wound insert 34 to wound 26.

Some embodiments of the present methods can also be understood with reference to FIGS. 3A and 3B. For example, some embodiments of the present wound-treatment methods comprise delivering a fluid to a wound (e.g., 26) through a wound dressing (e.g., 18) comprising a wound insert comprising a reactive agent deposited on or in the wound dressing such that the fluid reacts with and/or causes at least a portion of the reactive agent to pass from the wound insert to the wound. In some embodiments, delivering a fluid comprises activating a fluid source (e.g., 248) that is coupled to the wound dressing to deliver the fluid to the wound through the wound dressing. Some embodiments further comprise applying negative pressure (e.g., after and/or simultaneously with delivering a fluid) to the wound through the wound dressing. In some embodiments, applying negative pressure comprises activating a vacuum source (e.g., 200) that is coupled to the wound dressing to apply the negative pressure to the wound through the wound dressing. Arrows in FIG. 3B indicate the flow of fluid (and reactive agent and/or a product of the reactive agent and the fluid) to and from wound surface 42 (e.g., through wound insert 34) such that the reactive agent (and/or a product of the reactive agent and the fluid) can kill microorganisms 28 to reduce and/or eliminate infection of wound 26.

Hypochlorous acid (HOCl) and hypochlorite ion (ClO—, which is also commonly referred to, generally understood to be synonymous with, and may be referred to interchangeably in this disclosure as, OCl—) are examples of effective antimicrobial agents for biocidal action. For example, HOCl is typically capable of killing a broad spectrum of microbes (e.g., fungus, bacteria, viruses, fungus, yeast, and the like); often in a relatively short period of time (e.g., is capable of killing greater than 99% of microbes within a period of less than 10 seconds). Such antimicrobial agents can be generated or formed by a combination of the present reactive agents and fluid (e.g., water and/or aqueous solution, such as, for example, saline solution) and may be more effective and/or more versatile than antibiotics and other commonly used antimicrobial agents used in wound treatment in the past. For example, antibiotics may be bacteria-specific such that testing may be required to determine a suitable antibiotic to use for a specific wound or infection; and/or such that antibiotics may have only limited effectiveness for individual wounds and/or infections (e.g., where testing is not performed and/or where a wound is infected with a plurality of different bacteria). Such testing may take as long as several days to determine an appropriate antibiotic, delaying treatment or selection of an effective antibiotic. Additionally, bacteria may develop resistance to antibiotics, such that antibiotics may have reduced effectiveness after an amount of time. Further, antibiotics are typically administered intravenously (systemically) such that antibiotics may kill beneficial bacteria (e.g., in a patient's digestive system) and/or may cause organ damage (e.g., to a patient's liver).

Experiments were performed for some of the present reactive agents (and/or resulting solutions) to investigate their antibacterial properties. In a first experiment, an even monolayer of Methicillin-resistant *Staphylococcus aureus* (MRSA) bacteria was spread across the surface of each of several petri dishes, and either a 30 µg control dose of Vancomycin, or an 8 mm×5 mm piece of sponge was placed on each petri dish. The pieces of sponge included: a piece of polyurethane foam coated with a silver (Ag), a piece of dry silicone foam, a piece of silicone foam impregnated with a Polyhexanide solution, a piece of silicone foam deposited with $Ca(ClO)_2$ salt, and a piece of silicone foam deposited with NaClO salt. After placement of the pieces of foam, saline was dropped onto the foams deposited with $Ca(ClO)_2$ and NaClO salts, respectively, Each petri dish was incubated for eighteen (18) hours at 37° C., and the clear area in which the bacteria had been killed (inhibition zone) was measured. The foam with NaClO resulted in an inhibition zone of approximately 1600 $mm^2$, and the foam with $Ca(ClO)_2$ resulted in an inhibition zone of approximately 800 $mm^2$. The next-closest was the one 30 µg control dose of Vancomycin, which resulted in an inhibition zone of 200 $mm^2$. In a second, similar experiment, the monolayer of bacteria was *E. Coli* instead of MRSA, and the remainder of the second experiment was substantially the same as the first. The results of the second experiment were also similar. The foam with NaClO resulted in an inhibition zone of approximately 1050 $mm^2$, and the foam with $Ca(ClO)_2$ resulted in an inhibition zone of approximately 800 $mm^2$. The next-closest was the polyurethane foam with silver, which resulted in an inhibition zone of approximately 100 $mm^2$. From these preliminary experiments, the inventors believe the present reactive agents and the resulting solutions to have effective antimicrobial properties. The reactive agents (and/or antimocrobial products of the reactive agents) of the present embodiments can be configured to have a broad-spectrum killing power that will kill a variety of microbes (e.g., fungus, bacteria, viruses, fungus, yeast, etc.). Additionally, the present reactive agents (and/or antimocrobial products of the reactive agents) can be delivered locally (preventing systemic damage or other side effects to organs and the like).

However, due to the reactivity of HOCl or OCl— with oxidizable organic substances, its utility in wound care applications has previously been limited. For example, some prior art methods of generating hypochlorous acid have required electrolysis of saltwater or the like (e.g., with expensive equipment at a patient's bedside). By way of another example, commercially available chemicals (e.g., bleach) have a hypochlorous acid concentration of 5% or greater, which is too high to permit medical uses (e.g., will cause cytotoxicity). Additionally, at suitable medical concentrations (e.g., 2-20 mM hypochlorous acid solutions), approximately 99% or more of the solution is water, such that shipping is more expensive and/or more difficult than necessary. Further, storage of hypochlorous acid solutions is difficult, as reactions with containers typically degrade or reduce the concentration of the solution. However, the present wound inserts can be deposited with reactive agents (have reactive agents deposited in the foam of the wound inserts) such that upon application of a fluid such as saline or water, OCl (and/or ClO⁻) is released (e.g., to form hypochlorous acid) and delivered to a wound for biocidal action.

Figures 4, 5:
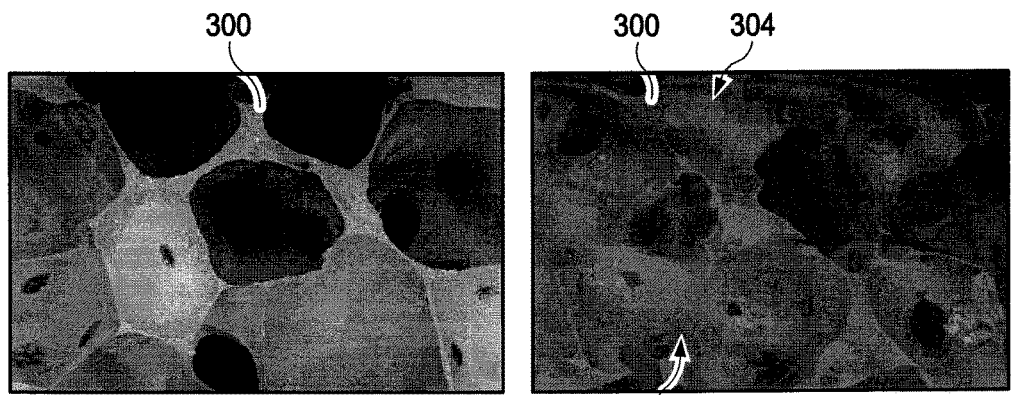
FIG. 4 depicts a photograph of a silicone foam suitable for some embodiments of the present wound inserts.
FIG. 5 depicts a photograph of a silicone foam deposited with Ca(OCl)$_2$ salt.

In the present embodiments, the foam and reactive agents can be selected such that the foam will not be degraded by the reactive agents (and/or products of the reactive agents and the fluid). The inventors of the present disclosure were surprised to discover the stability of the present silicone foams because testing with silicone tubes resulted in degradation of the hypochlorous acid and/or hypochlorite ion. However, the present silicone foams were compatible with the hypochlorous acid solutions (e.g., 0.1% hypochlorous acid solution), as discussed in this disclosure. For example, FIG. 4 depicts a photograph of a silicone foam 300 suitable for some embodiments of the present wound inserts, and FIG. 5 depicts a photograph of silicone foam 300 deposited with particles 304 of $Ca(OCl)_2$ salt. Foam 300 shown in FIG. 5 is an open-celled foam that is inert and stable in the presence of the $Ca(OCl)_2$ salt particles 304 such that foam 300 can be pre-deposited with the reactive agent, and shipped and/or stored without degradation of the reactive agent and/or without degradation of the foam; and such that foam 300 provides distribution channels or manifolds to permit dispersion of generally non-reactive fluids such as saline through foam 300 to dissolve and/or release the reactive agent (e.g., NaOCl salt, $Ca(OCl)_2$ salt, etc.) and deliver the reactive agent, and/or a reaction product of the reactive agent and fluid, to the wound. For example, in FIG. 5, the Ca(OCl)$_2$ salt particles are shown encapsulated in a suspension agent comprising polycaprolactone (PCL). In some embodiments, the reactive agent and/or the suspension agent are in dry and/or particle form. In other embodiments, the reactive agent and/or the suspension agent can be in a gel and/or droplet form. Examples of suitable silicone foams are available from Rogers Corporation, in Rogers, Conn., U.S.A. (certain product lines recently acquired from MTI Global, Inc., in Mississauga, Ontario, CANADA; and/or MTI Specialty Silicones, in Richmond, Va., U.S.A.), including for example, foams marketed as MagniFoam MF1-6535, MagniFoam MF1-8055, and/or MagniFoam MF1-9575.

Embodiments of the present wound inserts can comprise any of a variety of suitable reactive agents (e.g., dry and/or anhydrous reactive agents). For example, in some embodiments, the reactive agent comprises a hypochlorite salt (e.g., a dry and/or anhydrous hypochlorite salt), and/or is configured to react with water to form release hypochlorite ion (e.g., a salt or the like, that when dissolved by a fluid, can react or combine with the fluid to release hypochlorite ion and may also form hypochlorous acid, such as, for example, depending on pH). As used in this disclosure, "dry" refers to the absence of free water molecules in the salt used for the reactive agent (e.g., H$_2$O molecules may be present in certain salt crystalline structures, but such H$_2$O molecules are not free). In some embodiments, the hypochlorite salt used to make the present wound inserts may have a free water content of less than 2% by weight or less than 2% w/v. In some embodiments, the reactive agent comprises a substance defined by M(OCl)n, where n=1 if M is K$^+$ (potassium), Na$^+$ (sodium), or LI$^+$ (lithium); and where n=2 if M is Ca$^{2+}$ (calcium) or Mg$^{2+}$ (magnesium). In some embodiments, the reactive agent comprises at least one of: an N-chloro taurine; an N,N-dichloro taurine; an N-halogenated amino acid; an N,N-dihalogenated amino acid; and/or a combination of any two or more of these. Some embodiments comprise (alternatively or additionally) an agent comprising a growth factor; a protein; a peptide; or a combination thereof.

In some embodiments, the reactive agent can be deposited onto and/or into the open-cell foam with a chemically compatible polymer suspension or binding agent, such as, for example, to encapsulate the reactive agent for controlled release, improve physical stability of the reactive agent in the foam, and/or bind or adhere the reactive agent to the foam. For example, in some embodiments, the wound insert comprises a suspension agent that includes at least one of: a polyvinylpyrrolidone, a polyethylene oxide (PEO), a polyvinyl acetate (PVA), a polyvinyl alcohol (PVOH), an ethylene vinyl alcohol (EVOH) copolymer, an ethylene styrene copolymer, polycaprolactone (PCL), polysorbate, and/or a combination of any two or more of these. In some embodiments, the suspension agent is configured to dissolve in the presence of a solvent. For example, the suspension agent can be water soluble. In some embodiments, the reactive agent is dispersed throughout at least a portion (up to all) of the foam (e.g., a volume of the foam). In some embodiments, the reactive agent is coupled to a side of the foam (e.g., a bottom side adjacent to the wound when the wound insert is disposed on the wound).

Embodiments of the present wound inserts can comprise any suitable foam that is inert, chemically stable, and/or resistant to degradation in the presence of the reactive agent (and/or a product of the reactive agent). For example, in some embodiments, the foam comprises a fluoropolymer (e.g., a fluoropolymer comprising at least one of: polytetrafluoroethylene (PTFE), polyvinylidene fluoride (PVDF), perfluoroalkoxy (PFA) polymer, fluorinated ethylene-propylene copolymer (FEP), and/or a combination of any two or more of these). In some embodiments, the foam comprises a polyolefin and/or a polyolefin copolymer, such as, for example, polyethylene vinyl acetate copolymer (EVA), polyethylene vinylalcohol copolymer (EVOH), polyethylene-propylene copolymer, polyethylene-hexene copolymer (e.g., an olefin comprising at least one of: ethylene, propylene, butene, pentene, hexene, heptene, or a combination of any of these).

The present wound inserts (e.g., comprising a foam deposited with a reactive agent) provides a relatively easy delivery system for delivering or instilling highly effective (but often generally unstable) antimicrobial agents to the wound site at controlled rates for effective infection prevention and/or control to expedite wound healing. The present wound inserts (pre-deposited with reactive agents) can eliminate the need for complex and/or expensive on-site solution generation (e.g., electrolysis solutions such as are offered by PuriCore), and/or can eliminate the need for shipping or storing pre-mixed aqueous antimicrobial solutions (which generally contain more than 99% water); and/or enables the use of antimicrobial solutions (which may generally be chemically unstable) with negative pressure wound therapy (NPWT), such as, for example, by mixing such solutions at the wound.

Referring now to FIGS. 6-13, several experiments were performed on various materials to develop data indicative of which materials would be suitable for foams, reactive agents, and suspension agents of the present wound inserts, and/or suitable for fluids for releasing and/or delivering reactive agents to a wound. Hypochlorite typically has a characteristic absorption wavelength at about 292 nm in the ultraviolet (UV) spectrum. As illustrated in certain of FIGS. 6-13, absorbance at 292 nm was used to quantify the presence of hypochlorite OCl—. To capture the total active chlorine, pH of a solution generally should be adjusted to 8 or higher to convert all hypochlorous acid into hypochlorite.

Figure 6A:
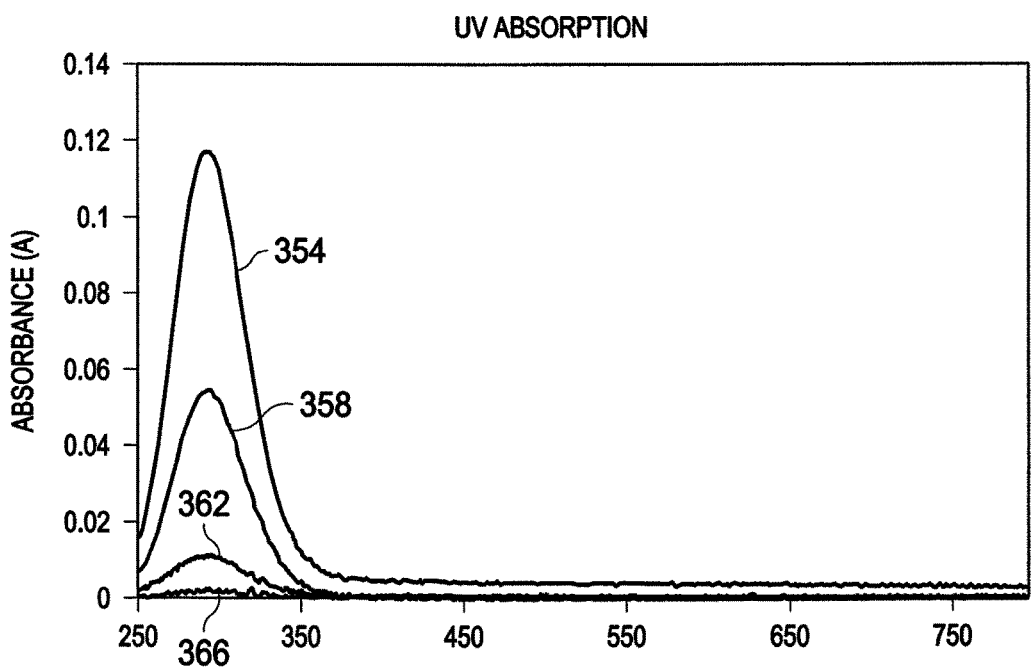
FIGS. 6A-6C illustrate certain characteristics of various components of the present wound inserts.

FIG. 6A depicts a chart of ultraviolet (UV) spectra of aqueous solutions of calcium hypochlorite Ca(OCl)$_2$ at various concentrations between 0 and 5 milliMolar (mM-0.001 moles per liter). More particularly, curve 354 corresponds to a solution having 0.56 mg of Ca(OCl)$_2$ per mL; curve 358 corresponds to a solution having 0.16 mg of Ca(OCl)$_2$ per mL; curve 362 corresponds to a solution having 0.032 mg of Ca(OCl)$_2$ per mL; and curve 366 corresponds to a solution having 0.0064 mg of Ca(OCl)$_2$ per mL. As illustrated, as the concentration of calcium hypochlorite in the solutions decrease, the absorption at 292 nm (generally corresponding to the concentration of hypochlorite OCl—) decreased.

Figure 6B:
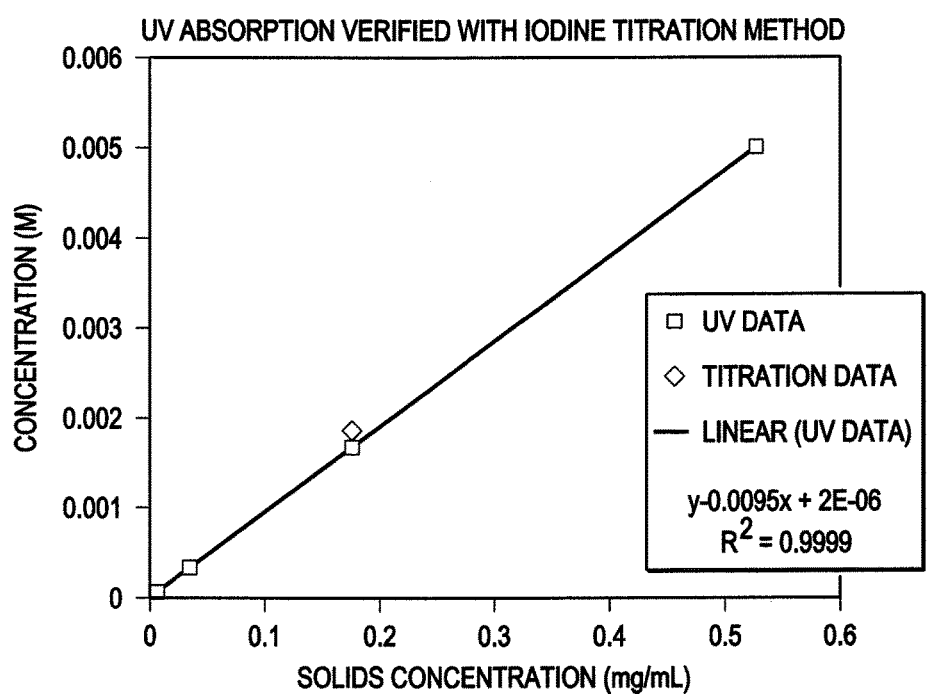
Figure 6C:
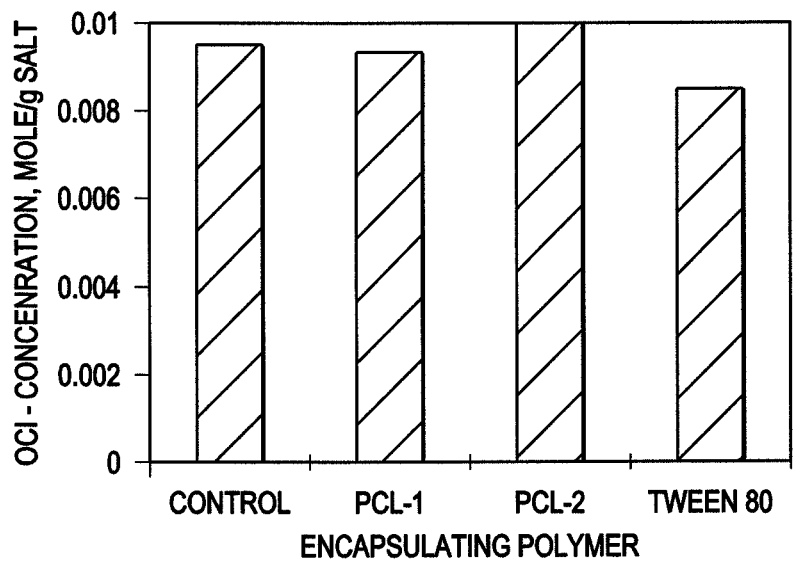

FIG. 6B depicts a chart illustrating the correlation of hypochlorite concentration from the UV absorbance of FIG. 6A with corresponding concentrations obtained by Iodine titration. FIG. 6C depicts a chart of OCl$^-$ concentration in solutions with certain of the present suspension agents, including a control of only Ca(OCl)2 in solution (of methylene chloride), Ca(OCl)$_2$ in PCL-1 solution having 0.5 g of PCL per 100 mL of methylene chloride; Ca(OCl)$_2$ in PCL-2 solution having 1.0 g of PCL per 100 mL of methylene chloride; and Ca(OCl)$_2$ in solution with TWEEN 80 (also known as polysorbate 80) having 0.1 g of TWEEN 80 per 10 g of methylene chloride. As indicated, the suspension agents did not substantially react with or otherwise consume or degrade the OCl$^-$. For each solution, approximately 13 mg of Ca(OCl)$_2$ was added to each methylene chloride solution and the solution was placed in the dark for a period of about one hour. Then 5 mL of distilled water was added to each solution, and each was shaken to mix its respective ingredients. The PLC-1 and PLC-2 solutions were allowed to sit for approximately five minutes to permit the contents to settle and separate into a PLC layer and an aqueous layer. The TWEEN 80 solution was allowed to sit for approximately two hours to permit the contents to settle and separate into a TWEEN 80 layer and an aqueous layer. After settling, for each solution, one milliliter of the aqueous layer was removed and mixed with 10 mL of 0.1 N NaOH (e.g., to increase the pH to ensure all hypochlorous acid is converted to hypochlorite for complete capture of active chlorine), and evaluated with UV-Vis spectroscopy to determine the concentration of OCl (e.g., to determine whether the OCl— had degraded or been consumed by the polymer). The test results verify that PCL and TWEEN 80 are compatible with $Ca(OCl)_2$ such that PCL or TWEEN 80 can be used as a suspension agent the $Ca(OCl)_2$ salt (e.g., to encapsulate or suspend the $Ca(OCl)_2$ salt).

Further details of certain examples of reactive agents and suspension agents are listed in Table 1. The Luvitec® K materials (e.g. Luvitec® K30, Luvitec® K90, etc.) are polyvinylpyrrolidones commercially available as powder or solution from BASF Corporation, Florham Park, N.J., U.S.A. Luvitec® VA64M is a vinylpyrrolidone/vinylacetate copolymer available from BASF Corporation, Florham Park, N.J., U.S.A. Chemlock® 607 is manufactured by LORD Corporation and is available from numerous distributors through the U.S.A. KBE-903 refers to 3-trimethoxysilylpropan-1-amine (CAS No. 86158-92-1; chemical formula $C_6H_{17}NO_3Si$). CF1-141 is a silicone (silane) primer available from numerous distributors throughout the U.S.A. P5200 Adhesion Promoter comprises: octamethyltrisiloxane, 1-Methoxyisopropyl orthosilicate, Tetrapropyl orthosilicate, and Tetrabutyl titanate, and is available from DOW Corning Corporation, Midland, Mich., U.S.A. 1205 Prime Coat comprises: Propylene glycol methyl ether; Toluene; Butyl glycol acetate; Bisphenol A, p-tert-butylphenol, (chloromethyl)oxirane polymer; and 2-Methoxypropanol; and is available from DOW Corning Corporation, Midland, Mich., U.S.A. 1200 RTV Prime Coat Clear comprises: Light aliphatic petroleum solvent naphtha; Xylene; Tetrapropyl orthosilicate; Tetrabutyl titanate; Tetra(2-methoxyethoxy) silane; Ethylene glycol methyl ether; and Ethylbenzene; and is available from DOW Corning Corporation, Midland, Mich., U.S.A.

TABLE 1

Examples of Suspension Agents, Properties, Applications, and Suppliers

| Binder | Material Properties | Application | Supplier |
|---|---|---|---|
| Poly(vinylalcohol) | Mw 124,000-186,00 | polymer | Aldrich |
| Polyvinylpyrrolidone | Mw 10,000 | polymer, gel | Aldrich |
| Poly(ethylene oxide) | Mw ~8,000,000 | polymer | Aldrich |
| Poly(vinyl alchohol-co-ethylene) | 44 mol % ethylene | polymer | Aldrich |
| KBE-903 | 3-Aminopropyltriethoxysilane | primer | ShinEtsu |
| Luvitec K30 | 30% solution | polymer, gel | BASF |
| Luvitec K90 | 20% solution, Brookfield viscosity 10,000-40,000 mPa s | polymer, gel | BASF |
| Luvitec VA64W | Vinylpyrrolidon Vinylacetate copolymer | polymer, gel | BASF |
| 1200 Clear RTV Prime Coat | Contains: naptha, tetrapropyl othosilicate, tetrabutyl titinate, ethylene glycol methyl ether, tetra(2-methoxyethoxy)silane, ethyl benzene | primer | DowCorning |
| 1205 Prime Coat | propylene glycol methyl ether, toluene, butylglycol acetate, bisphenol A, p-tert-butylphenol, (chloromethyl)oxirane polymer, 2-methoxypropanol | primer | DowCorning |
| P5200 Adhesion Promoter | octamethyltrisiloxane, tetrabutyl titanate, 1-methoxyisopropylorthosilicate, tetrapropylorthasilicate, n-butyl alcohol | primer | DowCorning |
| CF1-141 Silicon Primer | Contains: IPA | primer | NuSil |
| Chemlok 607 | Contains: MeOH, EtOH | primer | Lord |
| Chitosan Low Mw | Brookfield viscosity 20,000 cps | polymer | Aldrich |
| Chitosan Medium Mw | Brookfield viscosity 200,000 cps | polymer | Aldrich |
| Poly(styrene-ran-ethylene) sufonate | 5% polymer solution in 1-propanol: styrene, 76 wt. %; sulfonated styrene units, 32-38%; vinyl silane crosslinking agent, <0.5% | gel | Aldrich |
| Polycaprolactone (PCL) | Mx 14,000; 45,000; or 80,000 | pellets | Aldrich |

Figure 7:
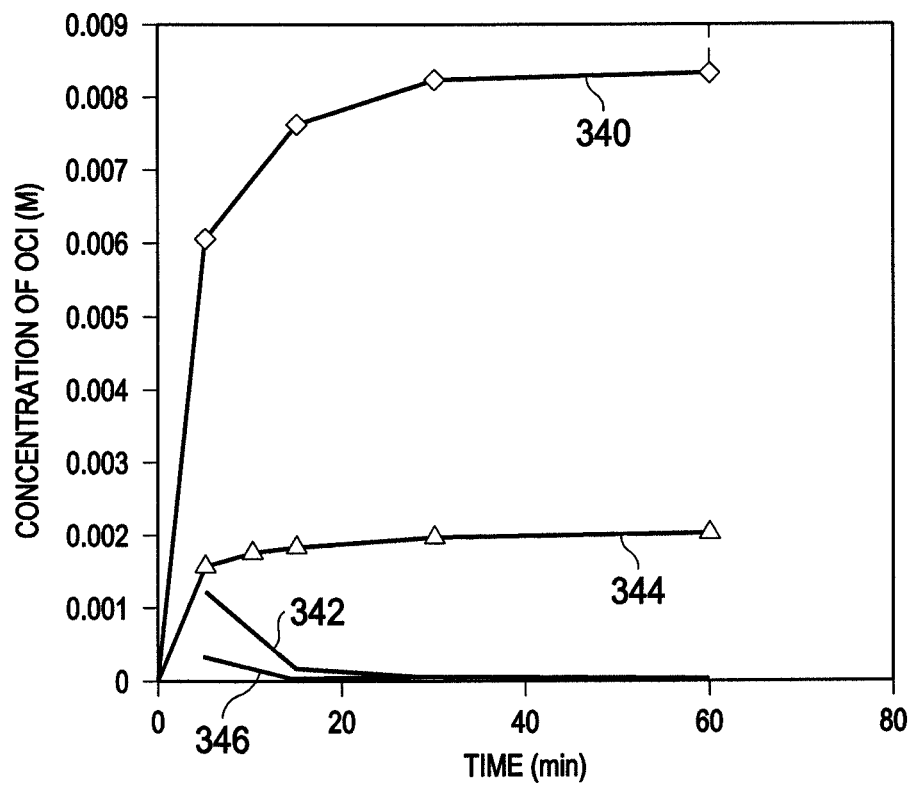
FIG. 7 depicts release profiles of silicone foam deposited with NaOCl salt.

FIG. 7 depicts release profiles of silicone foam (rectangular pieces of silicone foam (measuring 4 inches×3 inches× 1.25 inches) deposited with NaOCl salt. Curve 340 shows the molar increase in concentration of NaOCl in 500 milliliters (mL) of saline solution corresponding to the accumulated release of NaOCl salt from a saturated silicone foam over a period of 60 minutes; and curve 342 shows the corresponding rate of release of NaOCl from the foam over the same 60-minute period. Additionally, curve 344 shows the molar increase in concentration of NaOCl in 500 mL of saline solution corresponding to the accumulated release of NaOCl salt from an unsaturated silicone foam over a period of 60 minutes, and curve 346 shows the corresponding rate of release of NaOCl in the unsaturated foam over the same 60-minute period.

Figure 8:
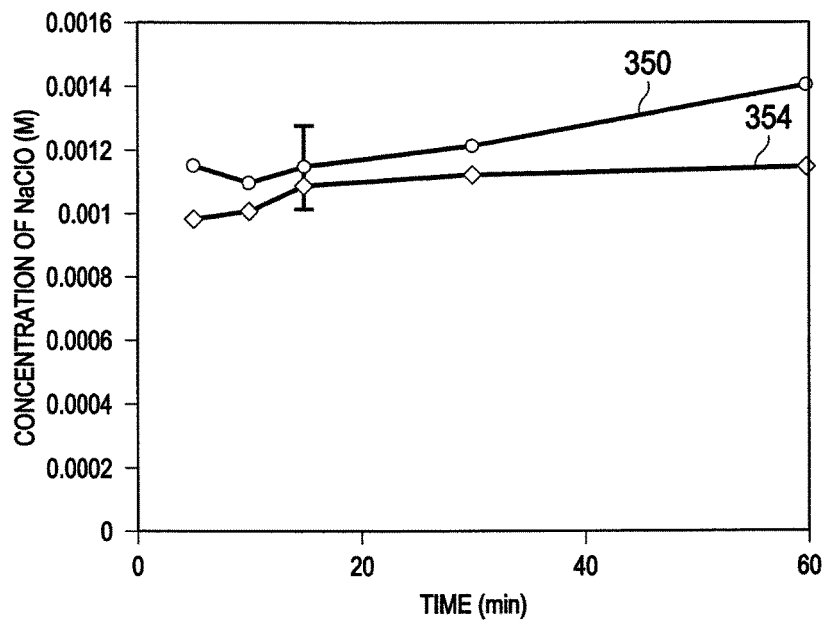
FIG. 8 depicts a release profile of silicone foam deposited with PEO/NaOCl.

FIG. 8 depicts a release profile of silicone foam (rectangular piece of silicone foam measuring 4 inches×3 inches× 1.25 inches) deposited with PEO/NaOCl (particles of a reactive agent comprising NaOCl, encapsulated in a suspension agent comprising polyethylene oxide (PEO)). More particularly, curve 350 shows the molar increase in concentration of NaOCl in 500 mL of saline solution, as measured by titration; and curve 354 shows the molar increase in concentration of NaOCl in 500 mL of saline solution corresponding to the release of NaOCl from the foam, as measured by UV-visible (UV-Vis) spectroscopy; both over a period of 60 minutes, as shown.

Figure 9:
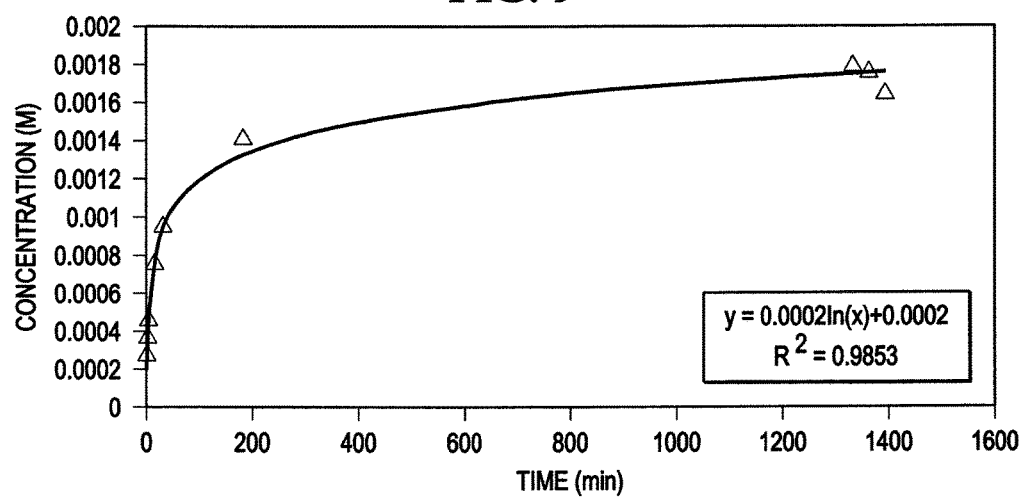
FIG. 9 depicts a release profile of silicone foam deposited with PCL/Ca(OCl)$_2$.

FIG. 9 depicts a release profile of PCL/$Ca(OCl)_2$ ($Ca(OCl)_2$ encapsulated in PCL). More particularly, 7.2 g of the PCL-1 solution described above with reference to FIG. 6C was placed in the bottom of a 500 mL glass beaker and allowed to dry overnight. Approximately 0.63 g of PCL/Ca (OCl)$_2$ remained once the fluid evaporated. Approximately 300 mL of saline solution at pH=4 was added to the beaker, and mechanically stirred to disperse the PCL/Ca(OCl)$_2$ in the saline. 1 mL aliquots were than removed from the beaker (at various time intervals between 1 and 1380 minutes), diluted with 10 mL of 0.1 NaOH (e.g., to increase the pH to ensure all hypochlorous acid is converted to hypochlorite for complete measurement by UV-Vis spectroscopy), and evaluated with UV-Vis spectroscopy to determine the molar concentration of hypochlorite ClO—, and the results plotted (FIG. 9) to approximate the release profile of Ca(OCl)$_2$ from the PCL suspension agent.

Figure 10:
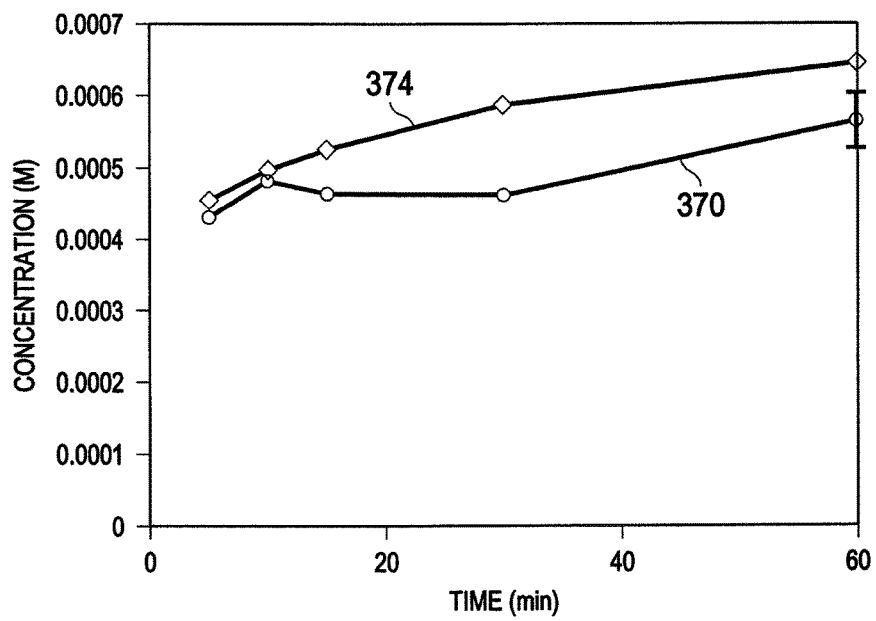
FIG. 10 depicts a release profile of foam deposited with Luvitec® K90/NaOCl.

FIG. 10 depicts a release profile, of a silicone foam deposited with Luvitec® K90/NaOCl (particles of a reactive agent comprising NaOCl encapsulated in a suspension agent comprising Luvitec® K90) released in two liters (L) of saline solution. More particularly, FIG. 10 depicts the release profile of the silicone foam (rectangular piece of silicone foam measuring 4 inches×3 inches×1.25 inches) deposited with Luvitec K90/NaOCl (a reactive agent comprising NaOCl encapsulated in a suspension agent comprising Luvitec® K90). More particularly, curve 370 shows the accumulated molar increase in concentration of NaOCl in 500 mL of saline solution, as measured by titration; and curve 374 shows the accumulated molar increase in concentration of NaOCl in 500 mL of saline solution corresponding to the release of NaOCl from the foam, as measured by UV-visible (UV-Vis) spectroscopy; both over a period of 60 minutes, as shown.

Figure 11:
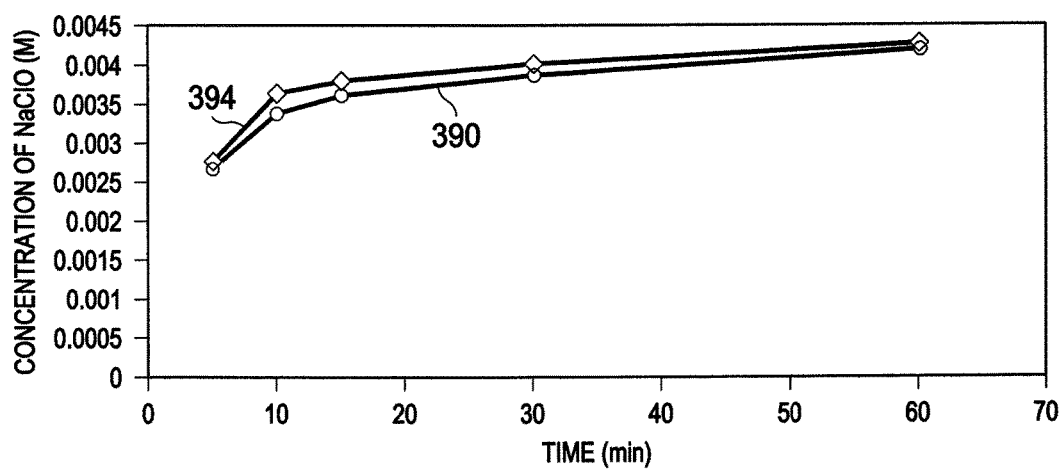
FIG. 11 depicts a release profile of foam deposited with PSES/NaOCl.

FIG. 11 depicts a release profile of a silicone foam deposited with the PSES/NaOCl (a reactive agent comprising NaOCl encapsulated in a suspension agent comprising PSES) in two liters (L) of saline. Details for the PSES are provided above in Table 1. More particularly, FIG. 11 depicts the release profile from a rectangular piece of silicone foam (measuring 4 inches×3 inches×1.25 inches) deposited with the PSES/NaOCl. More particularly, curve 390 shows the molar increase in concentration of NaOCl in 500 mL of saline solution, as measured by titration; and curve 394 shows the molar increase in concentration of NaOCl in 500 mL of saline solution corresponding to the release of NaOCl from the foam, as measured by UV-visible (UV-Vis) spectroscopy; both over a period of 60 minutes, as shown.

Figure 12A:
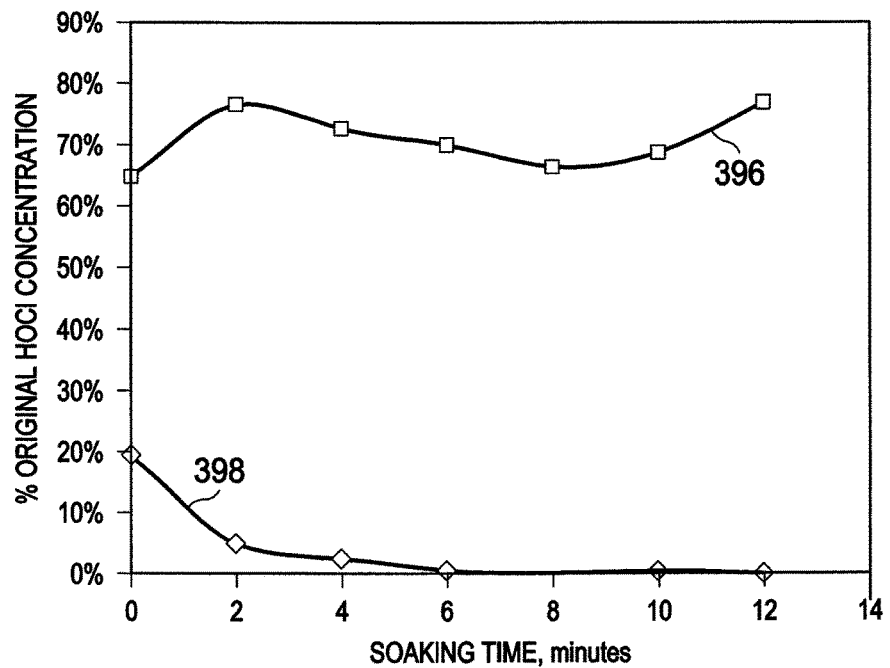
FIGS. 12A and 12B depict charts of stability data for hypochlorous acid solutions in various foams.
Figure 12B:
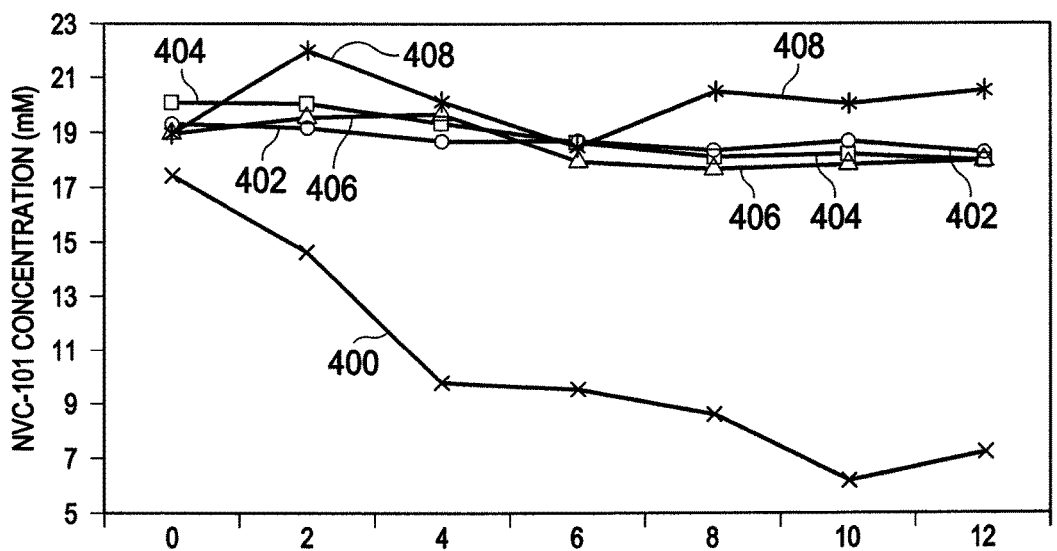

FIGS. 12A-12B depict charts of stability data for various foams soaked in hypochlorous acid solution. FIG. 12A illustrates HOCl concentration over time relative to initial HOCl concentration in a solution (initially 10 mM HOCl solution) passed through silicone foam (curve 396) and passed through polyurethane foam (curve 398) using a wound treatment system such as a VAC Instill device available from KCI. As shown, the polyurethane foam reacted with the HOCl to reduce the HOCl concentration in the solution, while the silicone foam was relatively stable such that the HOCl concentration remained relatively constant over the 12-minute test period. For FIG. 12B, various foams were soaked in 0.1% hypochlorous acid (HOCl) solutions for 12 minutes. Curves 400-410 show concentration of HOCl (e.g., fluctuations in concentration due to reaction with the foam) for several foams, such that the greater the reduction in concentration, the less stable the foam. Curve 400 shows the concentration over time for a polyurethane foam; curve 402 shows the concentration over time for MF1-6535, a silicone foam; curve 404 shows the concentration over time for MF1-8055, a silicone foam; curve 406 shows the concentration over time for MF1-9575, a silicone foam; and curve 408 shows the concentration over time for Virgin HOCl in a glass bottle for control (baseline and comparison) purposes. As shown, the polyurethane foam degraded in the hypochlorous acid solution, while the silicone foams were relatively stable.

FIGS. 13A-13E depict photographs illustrating tests performed on various foams to determine stability or physical integrity of the foams in hypochlorous acid solution. FIG. 13A depicts an experimental apparatus 450 used to evaluate stability or physical integrity of each of the foams evaluated for FIG. 11 through a number of cycles over a period of five days. Apparatus 450 is similar to the wound dressing 18 shown in FIGS. 1 and 3B, in that apparatus 450 includes a foam wound insert 454 covered by a drape 38, and in communication with a fluid source via connection pad 54a, and in communication with a vacuum source via connection pad 54b. An apparatus 450 was configured for the PU foam, and each of the silicone foams referenced above for FIG. 12B. The fluid source and vacuum sources were each sequentially activated repeatedly over a five-day period for each of the foams to deliver and remove a 0.1% hypochlorous acid solution to each of the foams. As shown in FIGS. 13B-13D, the silicone foams remained stable for the exposure. As shown in FIG. 13E, polyurethane foam collapsed and disintegrated as a result of oxidation.

Figure 14:
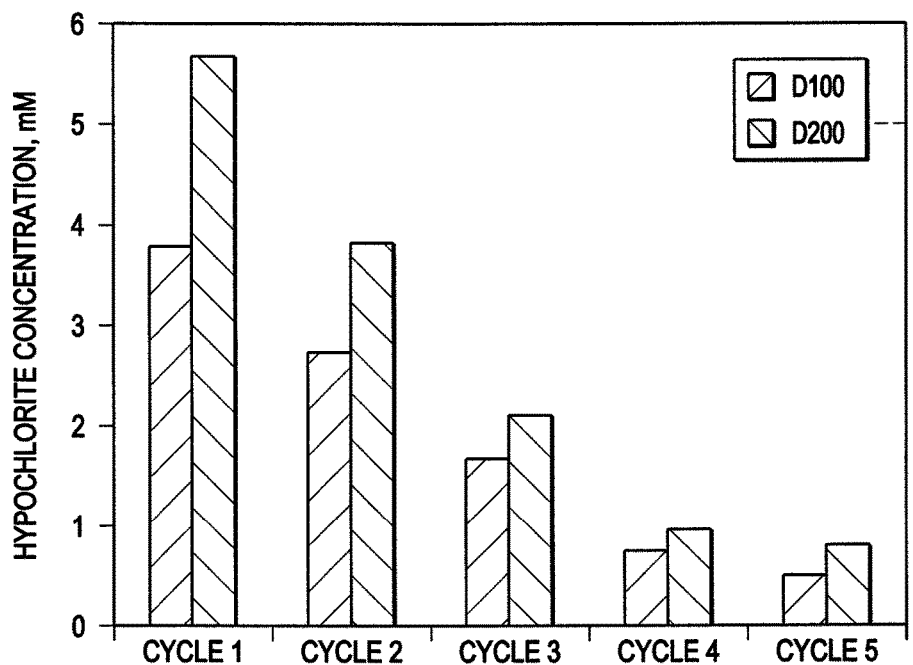
FIG. 14 depicts a chart of hypochlorite concentration (at various times) over multiple cycles of instilling saline solution through one of the present wound inserts at two different hold times for each cycle.

FIG. 14 depicts a chart of hypochlorite concentration at various times over multiple cycles of saline solution through one of the present wound inserts. For the chart shown, a suspension (or binding) agent, PCL (Mw 80,000), was mixed with Dichloromethane (DCM or methylene chloride) to form a 10% w/v PCL/DCM solution. Ca(OCl)$_2$ was then mixed into the PCL/DCM solution to form a slurry (Ca (OCl)$_2$ is generally not soluble in DCM). An oval-shaped piece of silicone foam having a volume of 12.05 cubic inches (in$^3$) was then placed in the PCL/DCM/Ca(OCl)$_2$ slurry and the foam alternately compressed and relaxed to draw the slurry into the foam, which resulted in a dispersion or loading of 0.63 grams of Calcium hypochlorite salt in the foam. Once the foam was substantially saturated, the foam was allowed to dry such that the DCM substantially evaporated from the foam to leave PCL-suspended (and/or PCL-encapsulated) Ca(OCl)$_2$ dispersed and deposited in the foam. The wound insert was then placed in an experimental apparatus 450 (FIG. 13A), and the experimental apparatus 450 was coupled to a VAC-Instill device commercially available from KCI for delivery/removal of fluids to/from the wound insert in the experimental apparatus. Normal saline solution (0.9% NaCl) was then delivered to the wound insert and the wound insert allowed to soak in the saline solution (e.g., to allow the saline solution to dissolve a portion of the Ca(OCl)$_2$ reactive agent to release hypochlorite ion in experimental apparatus 450. Each cycle included: activating a pump for 40 seconds to deliver the saline solution to the wound insert, allowing the wound insert to soak in the saline solution for 14 minutes, measuring the concentration of hypochlorite in the experimental apparatus 450 at various periods during the 14-minute soak period, and activating a vacuum source for 5 minutes to draw at least a portion the fluid out of the wound insert. This sequence was repeated 5 times (5 cycles). The hypochlorite concentrations for each cycle are shown in FIG. 14, with the hypochlorite concentration at 6 minutes into the soak period shown by the left bar, and the hypochlorite concentration at 12 minutes into the soak period shown by the right bar. As is shown, the hypochlorite concentration increases with soaking time, but decreases over multiple cycles. The suspension (or binding) agent (e.g., PCL) can be configured to permit the controlled release of an effective (e.g., antimocrobially effective) dose of the reactive agent, while still permitting substantially all of the reactive agent to be flushed from the wound insert over multiple cycles, thus reducing potential for long-term tissue damage that may otherwise result from the sustained or un-dissipating presence of reactive agents.

Figure 15:
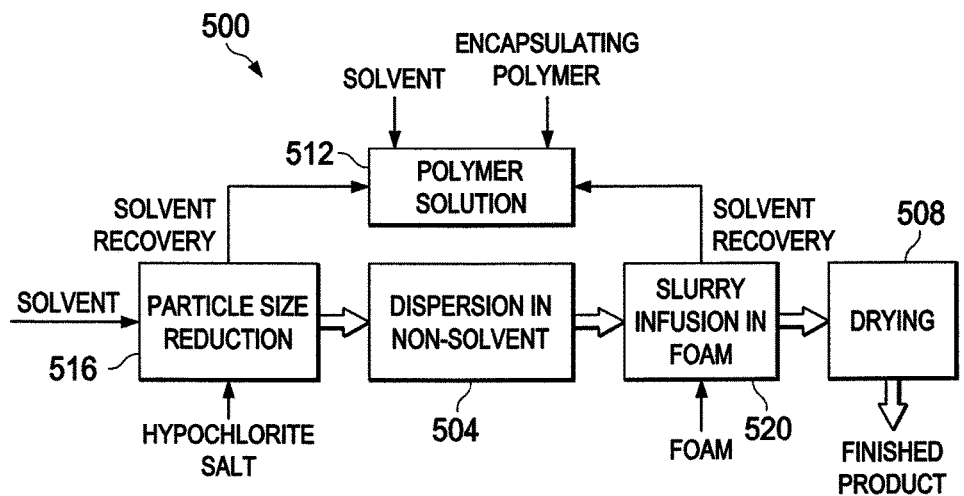
FIG. 15 depicts a flowchart of one of the present methods.

FIG. 15 depicts a flowchart conceptually illustrating an embodiment 500 of the present methods of manufacturing the wound insert tested to obtain the data of FIG. 14. In the embodiment, shown, the method comprises a step 504 of adding dry hypochlorite salt particles to a solution containing dissolved binding and/or encapsulating agent (e.g., polymer) such that the solution and hypochlorite salt form a slurry. Calcium hypochlorite (and other hypochlorite) salts are commercially available from a variety of sources. For example, Calcium hypochlorite is available from Sigma-Aldrich, PPG Industries, and Arch Chemicals, Inc. Such Calcium hypochlorite salts are also available with a range of available Chlorine contents (e.g., 34%-76%). In some embodiments, the hypochlorite salt has an available Chlorine content of 50% or more (e.g., at least 60%, at least 70%, or more). Other examples of hypochlorite salts are defined by M(OCl)n, where n=1 if M is $K^+$, $Li^+$, or $Na^+$, and where n=2 if M is $Mg^{2+}$.

In some embodiments, the solution comprises a polymer (binding agent and/or encapsulating agent) and a liquid that is a solvent of the polymer but not a solvent of the hypochlorite salt. For example, in the embodiment shown, the polymer is PCL. In other embodiments, the polymer can be another suitable biocompatible (e.g., biodegradable) polymer that is not water-soluble. For example, in the embodiment shown, the liquid is non-aqueous and comprises Dichloromethane (DCM or methylene chloride). In other embodiments, the liquid comprises a different non-aqueous solvent of the polymer (e.g., Tetrahydrofuran (THF) or Cyclohexane for PCL). The concentration of polymer in the liquid can be, for example, between 5% w/v and 10% w/v. For example, a concentration of 7% w/v (which may in some embodiments be between 6% and 8%) has worked well for certain experiments described below. In the embodiment shown, method 500 further comprises a step 508 of substantially removing the liquid from the slurry such that at least a portion of the hypochlorite salt particles are at least partially encapsulated by the polymer. For example, removing the liquid may be performed by drying (e.g., in vacuum and/or at ambient pressure). In the embodiment shown, all references to "solvent" are to DCM, which is also noted as a "Non-solvent" at step 504 because DCM is not a solvent for Ca(OCl)2 (e.g., Calcium Hypochlorite is generally not soluble in DCM).

In some embodiments, method 500 comprises a step 512 of forming the solution by combining the liquid and the polymer (to dissolve the polymer in the liquid). In some embodiments, method 500 comprises a step 516 of reducing, prior to adding the hypochlorite salt particles into the solution, the size of the hypochlorite salt particles such that a majority of the hypochlorite salt particles have a size at or below a target size. For example, for certain silicone foams discussed in this disclosure, the pore size is such that a target size of 180 microns permits adequate dispersion of the salt particles through the foam. For example, in some embodiments of commercially available $Ca(OCl)_2$, the average particle or aggregate size is approximately 1 millimeter (MM), and average particle size is reduced by disposing hypochlorite particles (e.g., pellets) into a slurry with Dichloromethane (DCM or methylene chloride) and shearing with a high-shear mixer (e.g., at 7000 rpm for 5 minutes, 7000 rpm for 7 minutes, 10000 rpm for 7 minutes, and/or other speeds or durations) to break larger particles into smaller particles. Particle size (e.g., the target size for a group of particles) may be adjusted for various applications of the present embodiments. For example, in a wound insert with hypochlorite salt at least partially encapsulated by PCL, larger salt particles will generally dissolve more slowly than smaller salt particles, and vice versa. In the embodiment shown, the solvent (DCM) is removed from the salt (or the salt is removed from the solvent) after reducing the particle size (e.g., may be filtered, evaporated, and/or otherwise recovered prior to introducing the hypochlorite salt particles into the solution).

In some embodiments, method 500 comprises a step 520 of disposing a foam wound insert in the slurry such that hypochlorite sale particles and polymer are dispersed within the wound insert, prior to step 508 of substantially removing the liquid. For example, the foam may be compressed and released one or more times in the presence of the slurry such that expansion of the foam will draw the slurry into the pores of the foam. The foam may be any suitable open-celled foam that is stable (will not degrade) in the presence of hypochlorite ion or hypochlorous acid (e.g., at least at concentrations present in the discussed embodiments). Examples of suitable foams include Silicone foams having a density in the range of 25-150 $kg/m^3$ (e.g., MagniFoam 6535, MagniFoam 8055, and MagniFoam 9575, manufactured by Rogers Corporation), Polyvinyl alcohol (PVOH), and the like.

Figure 16:
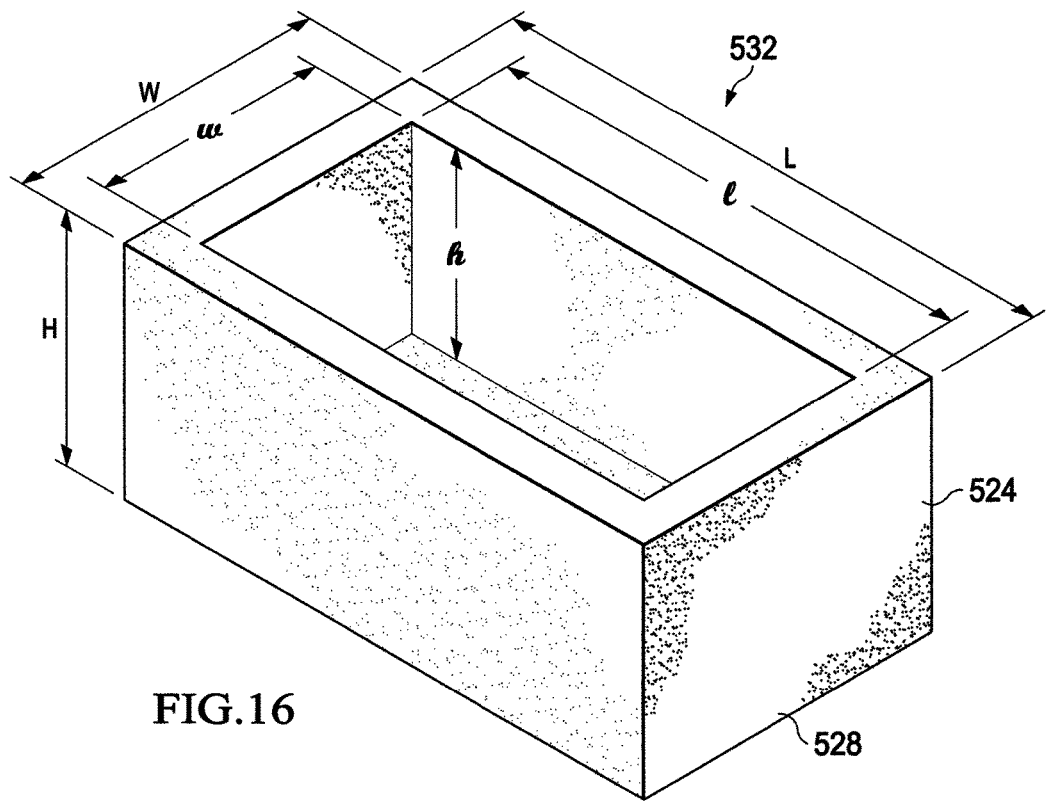
FIG. 16 depicts a housing suitable for use in certain embodiments of the present methods.

In some embodiments, step 520 may be accomplished with the apparatus 524 of FIG. 16. Apparatus 524 includes a body 528 defining a chamber 532 sized to receive a piece of foam to be used for a wound insert. The polymer/solvent/salt slurry and the foam can be disposed in chamber 532, and the foam compressed and permitted to expand to draw the slurry into the pores of the foam (e.g., can be sequentially compressed and allowed to expand multiple times). In some embodiments, the foam is compressed in the chamber with a plunger (not shown) having openings therethrough (and/or corresponding in shape to the chamber). Chamber 532 can be sized to correspond to a single wound insert, can be sized to correspond to a larger piece of foam from which multiple wound inserts can be cut after being infused with the slurry. Other embodiments may include multiple cavities each corresponding to a single wound insert. For example, the data shown in FIG. 14 was obtained with a mold having cavity dimensions of l=4.5 inches×w=3.5 inches×h=2 inches. Although not shown in FIG. 16 for simplicity, the inside corners of cavity 532 were also filleted (rounded) on radiuses of 0.5 inches. For other sizes of individual wound inserts, the cavity may be provided with any suitable dimensions (e.g., l=3.5 inches×w=3.5 inches×h=2 inches).

In some embodiments, the slurry is dispersed into the foam such that once the solvent is removed and the foam dried, the hypochlorite salt concentration in the foam is between 0.03 and 0.2 grams per cubic inch (g/in$^3$). For example, to generate the data of FIGS. 14 and 17, a 4-inch×3-inch×1.25-inch oval-shaped piece of foam was used having a volume of 12.05 cubic inches (in$^3$), and between 0.5 and 2.0 grams of Calcium hypochlorite salt were infused into the foam for various iterations. The concentration of hypochlorite per cubic inch of foam can be increased or decreased to vary the release profile of hypochlorite ion from the foam, and may vary for different foams and/or polymers (binding/encapsulating agents).

Figure 17:
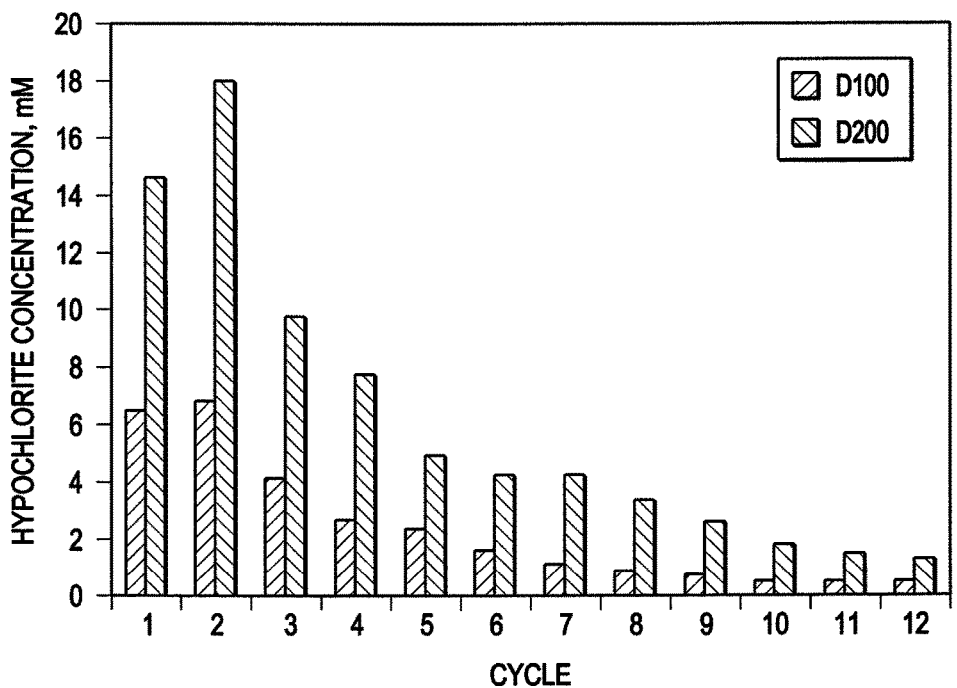
FIG. 17 depicts a chart of hypochlorite concentration for two different concentrations of calcium hypochlorite in a wound insert over multiple sequential cycles.

Referring now to FIG. 17, the experiments described above for FIG. 14 were also performed with additional foams, one foam in which 1 gram of Calcium hypochlorite salt was infused (D100, shown as left column for each cycle), and one foam in which 2 grams of Calcium hypochlorite salt was dispersed (D200, shown as right column for each cycle). As shown in FIG. 17, a single foam wound insert released enough hypochlorite ion to cause the liquid to have a concentration of hypochlorite ion in each of twelve sequential cycles between 0.5 and 18 mM. As discussed additionally below, the minimum concentration is significant because testing identified concentrations of hypochlorite-ion as low as 0.5-0.7 mM to have effective antibacterial and antimicrobial properties. Additional testing was performed to measure the zone of inhibition (ZOI) and Log Reduction of microbes for various samples of released aqueous solutions having various concentrations of hypochlorite ion, as listed in Tables 2 and 3. Table 2 lists ZOI and Log reduction data for a single cycle measured at hold times (exposure duration) of 30 seconds and 5 minutes of bacterial exposure to solution. Table 3 lists ZOI and Log reduction data for multiple cycles (each cycle including introduction of hypochlorite solution, and removal of solution prior to beginning next cycle). In the ZOI experimentation, foam discs having a diameter of 8 millimeters (mm) and a height of 5 mm were each saturated with hypochlorite-ion solution as indicated. Table 3 also lists the initial microbe count in log form (10$^X$, where X is listed in Table 2), log reduction in microbe count, and ZOI in mm. For the data of Table 3, the initial concentration (1×) of hypochlorite ion in solution was 5.7 mM of hypochlorite ion, which corresponds to 0.041% w/v of Ca(OCl)$^2$. In the Log reduction experimentation, the microbes were exposed to the respective concentration of solution for 30 seconds per cycle. It was observed that five (5) cycle sat even the lowest concentration (0.7 mM) killed substantially all microbes present. The bold entries in Table 3 are indicative of substantially all microbes being killed. In the biofilm eradication cycles listed in Table 6 below, probes were cultured with microbes and incubated to permit formation of a biofilm on the probe. The probe was then exposed to solutions having various concentrations of Calcium hypochlorite solution for multiple cycles, with each cycle including exposure of the probe to solution for a duration of 5 minutes.

TABLE 2

ZOI and Log Reduction Data for OCl$^-$ Solutions

| HOCl/OCl– | ΔLog - MRSA | | ΔLog - C. alb. | | ZOI, D in mm | |
|---|---|---|---|---|---|---|
| mM | 30 sec. | 5 min. | 30 sec. | 5 min. | MRSA | C. alb. |
| 15.7 | >6.93 | >7.13 | 3.50 | >7.18 | 13.0 | 44.3 |
| 10.7 | >6.93 | >7.13 | 7.18 | >7.18 | 13.0 | 45.7 |
| 4.0 | 5.52 | >7.13 | 3.94 | >7.18 | 0.0 | 34.3 |
| 3.1 | 3.55 | >7.13 | 3.08 | >7.18 | 0.0 | 22.0 |
| 1.9 | 2.93 | 4.09 | 2.94 | 3.77 | 0.0 | 24.3 |
| 0.8 | 2.96 | 2.99 | 2.87 | >7.18 | 0.0 | 15.0 |
| Microbe Count | 7.93 | 8.13 | 8.18 | 8.18 | — | — |

TABLE 3

ZOI and Log Reduction Data for OCl$^-$ Solutions

| Sample | *Pseudomonas aeruginosa* ATCC 27853 | | | *Staphylococcus aureus* ATCC 10832 | | | *Staphylococcus aureus* USA 400 (MRSA) | | |
|---|---|---|---|---|---|---|---|---|---|
| Dilution | 1 Cycle | 3 Cycles | 5 Cycles | 1 Cycle | 3 Cycles | 5 Cycles | 1 Cycle | 3 Cycles | 5 Cycles |
| 1x | −0.16 | 5.87 | 5.83 | 3.21 | 2.82 | 2.66 | 4.15 | 3.63 | 3.91 |
| 2x | −0.98 | 5.87 | 5.83 | 3.21 | 2.82 | 2.66 | 4.15 | 3.63 | 3.91 |
| 4x | −0.48 | 3.92 | 5.83 | 3.21 | 2.82 | 2.66 | 4.15 | 3.63 | 3.91 |
| 8x | −1.11 | 1.26 | 5.39 | 3.21 | 2.82 | 2.66 | 4.15 | 3.63 | 3.91 |

As illustrated by the data in Table 2 and Table 3, the minimum inhibitory concentration (MIC), minimum bactericidal concentration (MBC), and minimum biofilm eradication concentration (MBEC) of hypochlorite ion in solution (e.g., the solution formed by the release of hypochlorite ion when aqueous solution is added to the impregnated foam) for each of *Pseudomonas aeruginosa* ATCC 27853, *Staphylococcus aureus* ATCC 10832, and *Staphylococcus aureus* USA 400 (MRSA), at each of 1 3, and 5 cycles, are listed in Tables 4, 5, and 6. 0.0051% w/v Ca(OCl)2 in water corresponds to 0.7 mM hypochlorite ion in water

TABLE 4

Minimum Inhibitory Concentration (MIC) (% w/v)

| Bacteria | 1 Cycle | 3 Cycles | 5 Cycles |
|---|---|---|---|
| *Pseudomonas aeruginosa* ATCC 27853 | <0.005% | <0.005% | <0.005% |
| *Staphylococcus aureus* ATCC 10832 | <0.005% | <0.005% | <0.005% |
| *Staphylococcus aureus* USA 400 (MRSA) | <0.005% | <0.005% | <0.005% |

TABLE 5

Minimum Bactericidal Concentration (MBC) (% w/v)

| Bacteria | 1 Cycle | 3 Cycles | 5 Cycles |
|---|---|---|---|
| *Pseudomonas aeruginosa* ATCC 27853 | <0.005% | <0.005% | <0.005% |
| *Staphylococcus aureus* ATCC 10832 | <0.005% | <0.005% | <0.005% |
| *Staphylococcus aureus* USA 400 (MRSA) | <0.005% | <0.005% | <0.005% |

TABLE 6

Minimum Biofilm Eradication Concentration (MBEC) (% w/v)

| Bacteria | 1 Cycle | 3 Cycles | 5 Cycles |
|---|---|---|---|
| *Pseudomonas aeruginosa* ATCC 27853 | >0.041% | 0.021% | 0.041% |
| *Staphylococcus aureus* ATCC 10832 | <0.005% | <0.005% | <0.005% |
| *Staphylococcus aureus* USA 400 (MRSA) | <0.005% | <0.005% | <0.005% |

In alternate embodiments (not shown), the polymer (PCL)/salt (Ca(OCl)$_2$) slurry can be formed into or added to alternate delivery structures (e.g., instead of dispersion in foam). For example, the liquid (e.g., Dichloromethane) can be partially removed, and the slurry can be extruded or otherwise formed (e.g., cast) into sheets or fibers with encapsulated hypochlorite salt that can be reacted with water to release hypochlorite ion and/or hypochlorous acid. Such sheets can be sized to be used for wound dressings, and used as wound dressings (e.g., in the systems and methods similar to those described above). Such fibers can be woven into mats or sheets that can be used as wound dressings (e.g., in the systems and methods similar to those described above). In other embodiments, the slurry can be deposited on substrates other than foams. For example, the slurry can be sprayed or "printed" (e.g., using known spraying or printing devices) onto wound dressings or other medical devices (e.g., onto a side of drape 38 that is configured to face a wound).

Figure 18:
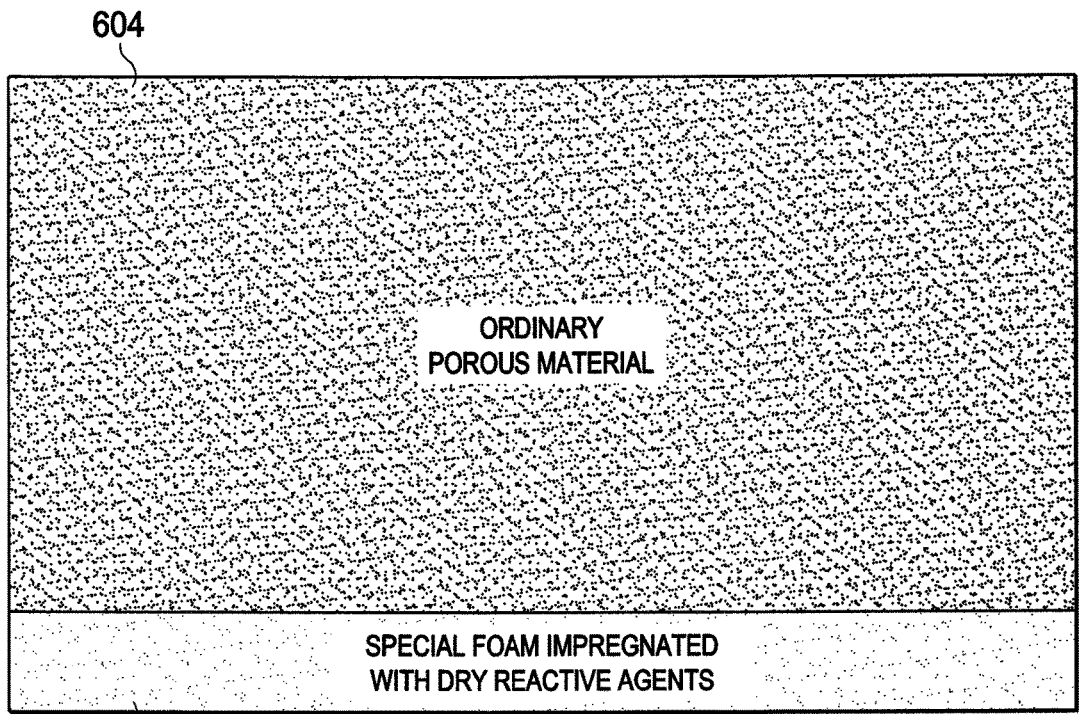
FIG. 18 depicts an alternate embodiment of one of the present wound inserts.

FIG. 18 depicts an alternate embodiment of one of the present wound inserts 34a that comprises an inert foam layer 600 that is deposited with a reactive agent (e.g., comprising any of the materials and/or components such as a suspension agent, as described above for wound insert 34); and a second open-celled foam layer 604 that is coupled to the first layer 600, and is not coupled to (not deposited with) the reactive agent. In accordance with the description above for the wound insert 34, the first open-celled foam 600 is configured to be inert in the presence of the reactive agent. Additionally, in the embodiment shown, foam 600 forms a first layer of wound insert 34a, and foam 604 forms a second layer of wound insert 34a.

Figure 19:
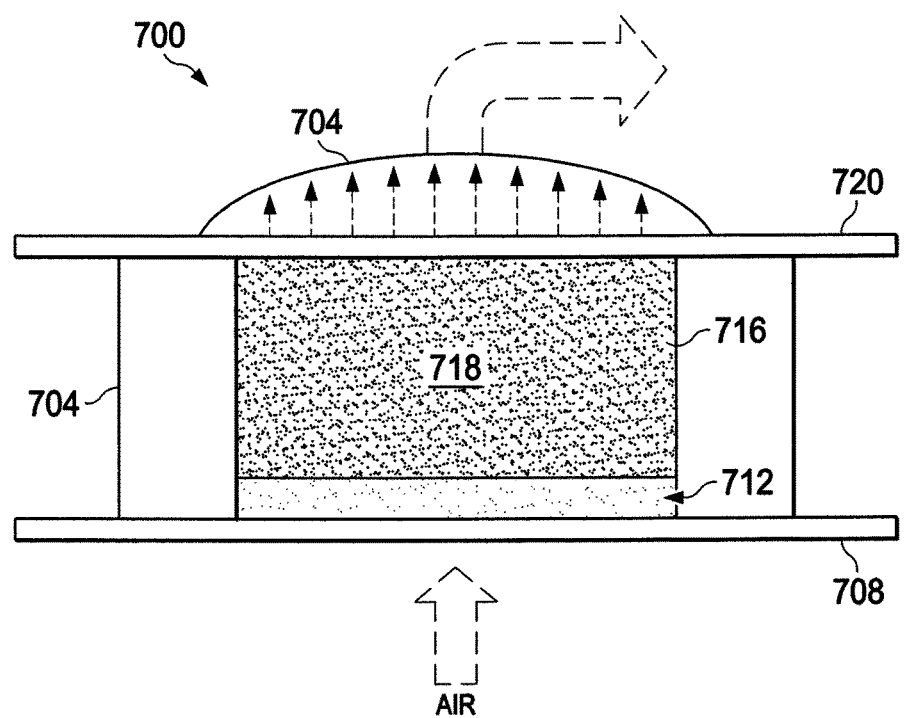
FIG. 19 depicts a cross-sectional side view of an apparatus for making some embodiments of the present wound inserts.

Referring now to FIG. 19, a cross-sectional side view of an apparatus 700 is shown for making some embodiments of the present wound inserts (e.g., wound insert 34). Apparatus 700 comprises a housing 704, a lower filter 708, a reservoir region 712, a foam region 716, an upper filter 720, and a vacuum manifold 724. Filters 708, 712 are coupled to housing 704, and are configured to permit air to pass through filters 708, 712, and to prevent particles of reactive agent from passing through filters 708, 712. Reservoir region 712 is configured to receive and/or be filled with particles (e.g., a predetermined amount or volume of particles or powder) of any of the reactive agents and/or suspension agents discussed in this disclosure. Foam region 716 is configured to receive a piece 618 of any of the foams discussed in this disclosure (e.g., a silicone or other inert foam). Once a reactive agent (and/or suspension agent) is disposed in reservoir region 712, a foam 718 is disposed in foam region 716, top filter 720 can be coupled to housing 704 to substantially enclose reservoir region 712 and foam region 716. Some embodiments of the present methods of forming a wound insert comprise: applying negative pressure (e.g., via vacuum manifold 714) to an open-celled foam (e.g., 718) to draw particles (e.g., of a reactive agent) into the foam such that the particles become dispersed throughout at least a portion of the foam.

In the embodiment shown, foam 718 has a first side (adjacent top filter 720) and a second side (adjacent reservoir region 712), and some embodiments of the present methods further comprise: disposing the foam between a filter (e.g., top filter 720) and a particle reservoir (e.g., reservoir region 712), where top filter 720 is configured to substantially prevent passage of the particles (of reactive agent and/or suspension agent) through top filter 720. In such embodiments, applying negative pressure can comprise: applying negative pressure to the filter (top filter 720) such that the particles (of reactive agent and/or suspension agent) are drawn from the reservoir (reservoir region 712) into the foam (e.g., 718) but are prevented from passing through the filter (top filter 720). In addition to the reactive agents described above, in some embodiments of the present methods of forming a wound insert, the particles comprise a metal (e.g., silver) such that the silver particles are drawn into the foam. These methods of forming the present wound inserts permit loading, dispersion, and/or deposition of reactive agents in foam without soaking the foam in a liquid solution and drying the foam to leave the solid agent in the foam. In contrast to prior methods, the present methods of vacuum loading is more efficient and can directly "charge" the foam with solid particles (e.g., powder). In some embodiments, the present wound inserts are configured to be disposed with the bottom side (side adjacent reservoir region 612) adjacent a wound, such that as fluid is introduced it will direct the particles in an opposite direction from the direction in which they were drawn into the foam.

In some embodiments of the present wound inserts, rather than dispersing a dry reactive agent in a foam, the foam is packaged in a wet state in which the foam contains a liquid containing a reactive agent. For example, WhiteFoam is a polyvinyl alcohol (PVOH) open-celled foam wound insert, currently available from KCl U.S.A., Inc., which is typically packed when the foam contains water in a moisture-barrier foil pouch to prevent evaporation of the water. In some embodiments, the present wound inserts comprise foam containing a liquid solution comprising antimicrobial agents (e.g., polyhexanide). In some embodiments, the present wound inserts comprise a container enclosing the wound insert and configured to prevent evaporation of the solution from the wound insert.

Figure 20:
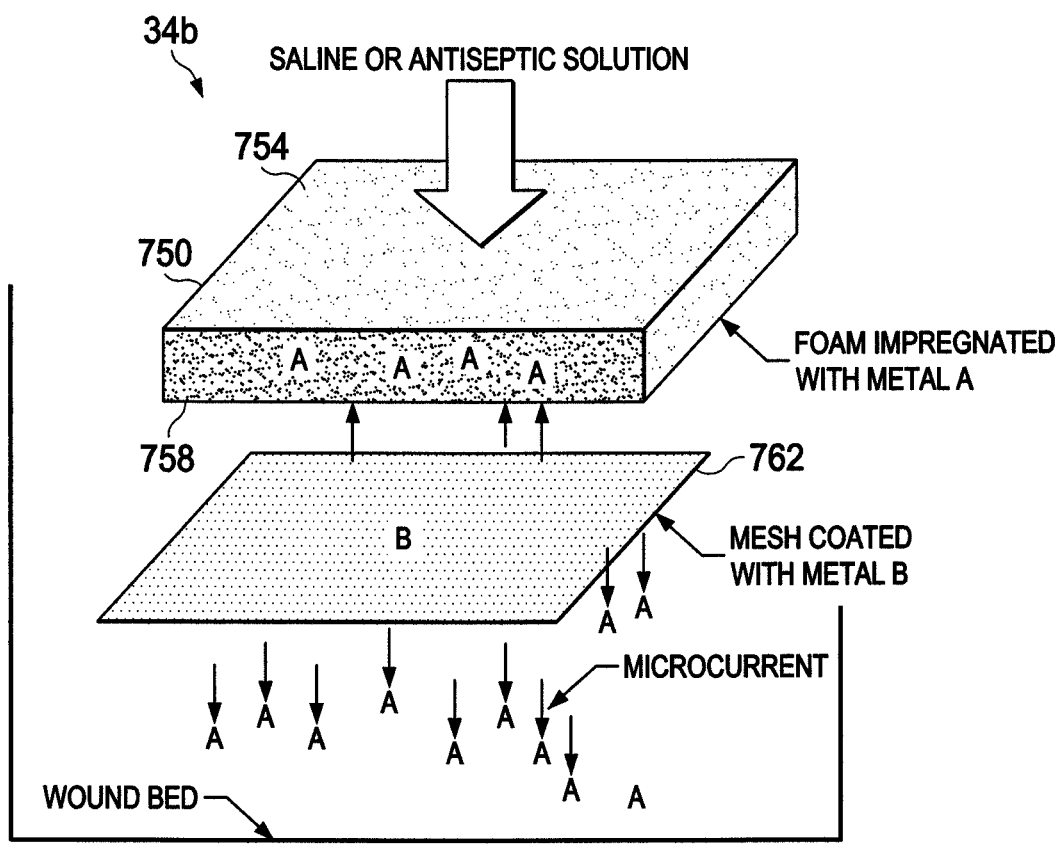
FIG. 20 depicts an exploded perspective view of another embodiment of the present wound inserts.

Referring now to FIG. 20, an exploded perspective view is shown of another embodiment 34b of the present wound inserts. In the embodiment shown, wound insert 34b comprises an open-celled foam 750 configured to be disposed between a wound (e.g., 26) of a patient (e.g., 30) and a drape (e.g., 38) coupled to skin (e.g., 46) of the patient such that the drape forms a space (e.g., 50) between the wound and the drape. Foam 750 has an upper side 754 and a lower side 758 that is configured to face the wound. In the embodiment shown, foam 750 comprises a plurality of particles A dispersed within foam 750, and a second metal B coupled to (e.g., coated on) lower side 758 of the foam. Additionally, foam 750 is configured such that a fluid can be introduced to generate microcurrents between first metal A and second metal B (e.g., such that upon introduction of fluid to the foam, microcurrents are generated between metal A and metal B). Additionally, in the embodiment shown, particles of first metal A are dispersed in foam 750 such that if a fluid passes through the foam at least some portion of first metal A will exit the foam. In some embodiments, first metal A and first metal B comprise anode and cathode materials. For example, in some embodiments, metal A comprises an anode metal and metal B comprises a cathode metal. By way of another example, in some embodiments, metal A comprises a cathode metal, and metal B comprises an anode metal. In some embodiments, first metal A comprises silver. In some embodiments, second metal B comprises zinc.

In the embodiment shown, wound insert 34b further comprises: a permeable layer (e.g., mesh) 762 coupled to lower side 758 of foam 750; where second metal B is coupled to permeable layer 762. Additionally, in the embodiment shown, wound insert 34b is configured such that if a fluid (e.g., water, saline, etc.) is passed through foam 750 from upper side 754 through lower side 758, at least some portion of first metal A will exit foam 750 through lower side 758 and pass through permeable layer 762 (e.g., to pass to a wound surface 42). For example, wound insert 34b is configured such that if wound insert 34b is disposed such that permeable layer 762 is in contact with a wound 26 (e.g., a wound surface 42) and a fluid is passed through foam 750 from upper side 754 to lower side 758, at least some portion of first metal A will exit the foam through permeable layer 762 and microcurrents will be generated between first metal A and second metal B coupled to permeable layer 762.

Wound insert 34b can thus be configured and/or used to provide microcurrents to a wound, such as, for example, to stimulate activities of extracellular matrix (ECM), growth factors, cells, and tissues to enhance tissue regeneration and wound healing process. Additionally, such microcurrents can make microorganisms and associated biofilms more susceptible to attack and destruction by a patient's immune system and/or antibiotics or antiseptics. For example, first metal A (especially free metal A that travels to a wound surface) and second metal B can act as electrodes (e.g., for $\Delta V \sim 1$ volt) to generate microcurrents within the wound bed.

The various illustrative embodiments of devices, systems, and methods described herein are not intended to be limited to the particular forms disclosed. Rather, they include all modifications and alternatives falling within the scope of the claims. The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified. The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems. It will be understood that the above description of embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

The invention claimed is:

1. A wound treatment apparatus, comprising:
   a wound insert comprising an open-celled foam;
   a reactive agent disposed within the foam, and configured to be inert in the absence of an activating fluid and to exhibit antimicrobial properties in the presence of an activating fluid;
   a drape configured to cover the wound insert; and
   a fluid delivery pad configured to be coupled to the drape and a fluid source, wherein the fluid source is actuatable to deliver a fluid to a wound through the wound insert;
   wherein the wound insert is configured to pass at least a portion of the reactive agent to a wound if the activating fluid is delivered to the wound insert.

2. The wound treatment apparatus of claim 1, further comprising a vacuum source configured to be coupled to the wound insert such that the vacuum source is actuatable to apply negative pressure to the wound insert.

3. The wound treatment apparatus of claim 1, wherein the reactive agent comprises a dry hypochlorite salt defined by M(OCl)n, where n=1 if M is $K^+$, $Li^+$, or $Na^+$, and where n=2 if M is $Ca^{2+}$ or $Mg^{2+}$.

4. The wound treatment apparatus of claim 1, wherein the open-celled foam comprises a silicone foam having a porosity sufficient for communicating negative pressure.

5. The wound treatment apparatus of claim 4, wherein the reactive agent comprises a dry hypochlorite salt defined by M(OCl)n, where n=1 if M is $K^+$, $Li^+$, or $Na^+$, and where n=2 if M is $Ca^{2+}$ or $Mg^{2+}$.

* * * * *